United States Patent
Fox et al.

(10) Patent No.: US 7,915,398 B2
(45) Date of Patent: Mar. 29, 2011

(54) MAIZE PROMOTER P67 AND METHODS OF USE

(76) Inventors: Timothy W Fox, Des Moines, IA (US); Yongzhong Wu, Johnston, IA (US)

(*) Notice: Subject to any disclaimer, the term of this patent is extended or adjusted under 35 U.S.C. 154(b) by 248 days.

(21) Appl. No.: 12/057,862

(22) Filed: Mar. 28, 2008

(65) Prior Publication Data

US 2008/0184388 A1    Jul. 31, 2008

Related U.S. Application Data

(62) Division of application No. 11/014,071, filed on Dec. 16, 2004, now Pat. No. 7,696,405.

(60) Provisional application No. 60/530,478, filed on Dec. 16, 2003, provisional application No. 60/591,975, filed on Jul. 29, 2004.

(51) Int. Cl.
*C12N 15/63*    (2006.01)
*C12N 15/82*    (2006.01)
*A01H 1/00*    (2006.01)

(52) U.S. Cl. .................. 536/24.1; 435/320.1; 800/287
(58) Field of Classification Search .................. None
See application file for complete search history.

(56) References Cited

OTHER PUBLICATIONS

Sequence alignment.*
Sequence alignment with SEQ ID No. 80898 of U.S. Appl. No. 20080034453 (2008).*

* cited by examiner

*Primary Examiner* — Li Zheng
(74) *Attorney, Agent, or Firm* — Pioneer Hi-Bred, Int'l, Inc

(57) ABSTRACT

A promoter isolated from *Zea mays*, designated the P67 promoter, provides a high level of specificity for expression in developing pollen, particularly at the mid-uninucleate stage, as confirmed by RT-PCR and Northern blot analyses of RNA samples from various tissues. Compositions and methods of use of the P67 promoter are disclosed.

10 Claims, No Drawings

SEQUENCE LISTING

```
<160> NUMBER OF SEQ ID NOS: 2

<210> SEQ ID NO 1
<211> LENGTH: 1112
<212> TYPE: DNA
<213> ORGANISM: Zea mays
<220> FEATURE:
<221> NAME/KEY: promoter
<222> LOCATION: (1)...(1112)
<223> OTHER INFORMATION: P67

<400> SEQUENCE: 1
gacgcgactg ctgacaaccc tagctagaaa caccctgaac actagttagg ttttcctctg      60
ttatctgcgt tgtcgatgta gttttcttta tctcgagcac cgatgtgcat ctgtgatcgg     120
gagatcatgt ctctggaaac tgttgtcttc gagatcctgt attaggagaa ggaaaataag     180 gttttgaga agcgtattca catgactact cacgttttcc ttgccatcga ccacgtcgtc      240
gaccctgcta gcttccacgt tgtcattcag tatgttcgat cgcatcatct gatctaatct     300
tataatgcag ttcatctgtt atggtagaag tgtgtcgcat tcttataatt agcatgttag     360
ggttacatgt taggtaacag acaccgagat tatctctgta caccattgtt gccttcattg     420
cctacgtcgt ctctcacagc cacaggtgtc tgaatcatga ccctcttttt aggagtagtc     480
tgtagagatg tgaggtaaag cagctttgca cgagaacgcc aatctcgcgt gtttccgagt     540
attttactgc tccatttgtg ggctacgcct gttgtttccg ccacggatgt cggctgctca     600
tcaccaaaaa tatgactact ttgaagttct ggtagcagag tgggcccaga cgccgttgct     660
tgattctggc tgggccaggc tacgtgaggc cttcttatta gatcatttcc gctgaaaggc     720
cgaaacgtga gagcctggca aacttttcta gaaaaaaaaa attcgcaaac aaaatttttt     780
ccgaacaaac gctacaccag tgaccgccgt ccgtcgtcgt tgcttggctc tcccttact     840 tcggctccaa cgccaatgca caaccgtccc tcttcgccat gtcccagttt tgacgctgcc     900
tgtagcgcag tataaaaaat cgtctcgatg ctcttgctcg gtactccaat tcacaccaaa     960
acatagagtg tcgactttc tattggtgtg attgggggca ctaaatacct accacattgc     1020
actcagacta catatactgt gtttgtgtgt tgtaagccgt aagcgtgtgt gagcttgcgc     1080
aaattggaca tctaggccgt gcgtaccctg cg                                    1112

<210> SEQ ID NO 2
<211> LENGTH: 1092
<212> TYPE: DNA
<213> ORGANISM: Zea mays
<220> FEATURE:
<221> NAME/KEY: promoter
<222> LOCATION: (1)...(1092)
<223> OTHER INFORMATION: P95

<400> SEQUENCE: 2
gcgacgtcga gatcacgaga ggctcgtacg gggacaacgc gctaggtctc ttagtcagat      60
```

-continued

```
cagttcaaat ctcttaattc ttgtcctcct tctcagtcca gttcttacat ctatctgtct      120
gatcccatta tttccaacac cacttgaacc aatctgctct gatgcccgt tcctgatgtt       180 gtcgtcgttg tcactttctc gacgtgcgtt gtcgtccgac cctgacccct tctcgatgcc      240
tcatctccga cagacgacga gtttagcaaa ccagcgagcg ttgattctct gccgaaaagg      300
ttgcctgacc ccgtctcctt cccgatggcc ctacacttcg agaagatcac cacttcgaga      360
agatcaccag atcaatatcc gaaaagatac acatagttta gattcagtca gcaaaaagct     420
aacattatgt ttgcttcttt tattcatata gttttcttag catgaaattt aaattctata     480
tagtactggt tttttacgag cttacttaat tttattaggg ctaatttggt aaccacattt     540
ttccacggaa tttcaatttt cctaaggaaa attagttaat tttcgcttgg gaaaatagaa     600
atttcatggg aaaatgcggt tcccaaacta gccttagcct tataggtttt ttttagccca     660
tgtgaattct cgtcaaaggg actcagtcca cttcacagca ggtgaggtgg tttttgaatg     720
cccaaataca gatctgttaa ttaattttca gagggtcagg acgcggtcgc ccgaacgggc     780
ggacgcgcga acaatccgcc cgcccgcgcg cgcgacctgc cacttcgggc catggccagc     840
acccagcatg cgtcgtccta aacgacgagc accgcccgtt ggcgctataa agccccgcct     900
cggcgtcccc ttgtcaattc gaagccttcc cggttacccc ttcggcctcc acctatcacc     960
acccgggacg tcttccaggg tctcctcgta gtagaatagc tctatctcac cgcaacaact    1020
cctcattaca tcctttagga gaggctgatc gattggtaga tacgtactcg ggtggagcag    1080
aacaacgaga ga                                                        1092
```

MAIZE PROMOTER P67 AND METHODS OF USE

This application is a divisional of U.S. patent application Ser. No. 11/014,071, filed Dec. 16, 2004, now U.S. Pat. No. 7,696,405, which claims priority to Provisional Application No. 60/530,478, filed Dec. 16, 2003, and Provisional Application No. 60/591,975, filed Jul. 29, 2004, all of which are hereby incorporated by reference.

BACKGROUND OF THE INVENTION

1. Field of the Invention

The invention relates generally to compositions and methods for dominant gene suppression. Certain embodiments provide methods for preventing transmission of transgenes in gametes. Certain embodiments comprise pairs of plants in which the phenotype of the parents is suppressed in the progeny. Certain embodiments provide constructs and methods useful for generating fertile parental plants that, when crossed, generate sterile progeny plants, and methods of making and using such transgenes and plants, as well as products of such plants.

2. Background Information

Plant breeding provides a means to combine desirable traits in a single plant variety or hybrid, including for example, disease resistance, insect resistance, drought tolerance, improved yield, and better agronomic quality. Field crops generally are bred by pollination, including by self-pollination (selfing; selfed), in which pollen from one flower is transferred to the same or another flower of the same plant, or to a genetically identical plant, and cross-pollination (crossing; crossed), in which pollen from one plant is transferred to a flower of a genetically different plant.

Plants that are selfed and selected for type over many generations become homozygous at almost all gene loci and produce a uniform population of true breeding progeny. A cross between two different homozygous lines produces a uniform population of hybrid plants that can be heterozygous at many gene loci. A cross of two plants, each of which is heterozygous at a number of gene loci, generates hybrid plants, which differ genetically and are not uniform.

Many crop plants, including, for example, maize (corn), can be bred using self-pollination or cross-pollination techniques. Maize has separate male and female flowers on the same plant, located on the tassel and the ear, respectively. Natural pollination occurs in maize when wind blows pollen from the tassels to the silks that protrude from the tops of the ears. Many crop plants, including maize, are grown as hybrids, which generally exhibit greater vigor than the parental plants from which they are derived. As such, it is desirable to prevent random pollination when generating hybrid plants.

Hybrid plants (F1) are generated by crossing two different inbred male (P1) and female (P2) parental plants. Hybrid plants are valued because they can display improved yield and vigor as compared to the parental plants from which the hybrids are derived. In addition, hybrid (F1) plants generally have more desirable properties than progeny (F2) plants derived from the hybrid plants. As such, hybrid plants are commercially important, and include many agricultural crops, including, for example, wheat, corn, rice, tomatoes, and melons. Hybridization of maize has received particular focus since the 1930s. The production of hybrid maize involves the development of homozygous inbred male and female lines, the crossing of these lines, and the evaluation of the crosses for improved agronomic performance. Pedigree breeding and recurrent selection are two of the breeding methods used to develop inbred lines from populations. Breeding programs combine desirable traits from two or more inbred lines, or various broad-based sources, into breeding pools from which new inbred lines are developed by selfing and selecting for desired phenotypes. These new inbreds are crossed with other inbred lines and the resultant new hybrids are evaluated to determine which have improved performance or other desirable traits, thus increasing commercial value. The first generation hybrid progeny, designated $F_1$, is more vigorous than its inbred parents. This hybrid vigor, or heterosis, can be manifested in many ways, including increased vegetative growth and increased seed yield.

Production of hybrid seed requires maintenance of the parental seed stocks because self-crossing of hybrid plants produces progeny (F2) that, like P1 and P2, generally exhibit less desirable characteristics than the F1 hybrid plant. Because the parental plants generally have less commercial value than the hybrids (F1), efforts have been made to prevent parental plants in a field from self-crossing ("selfing"), since such crosses would reduce the yield of hybrid seed. Accordingly, methods have been developed to selfing of a parental plant.

One method for controlling pollination is to use a parental population of plants that are male sterile, thus providing the female parent. Several methods have been used for controlling male fertility, including, for example, manual or mechanical emasculation (detasseling), cytoplasmic male sterility, genetic male sterility, and the use of gametocides. For example, parental selfing in a field can be prevented by removing the anthers or detasseling plants of the female parental (P2) population, thus removing the source of P2 pollen from the field. P2 female plants then can be pollinated with P1 pollen by hand or using mechanical means. Hybrid maize seed generally is produced by a male sterility system incorporating manual or mechanical detasseling. Alternate strips of two maize inbreds are planted in a field, and the pollen-bearing tassels are removed from one of the inbreds (P2 female). Provided that the field is sufficiently isolated from sources of foreign maize pollen, the ears of the detasseled inbred are fertilized only by pollen from the other inbred (P1 male); resulting seed is hybrid and forms hybrid plants. Unfortunately, this method is time- and labor-intensive. In addition, environmental variation in plant development can result in plants producing tassels after manual detasseling of the female parent is completed. Therefore detasseling might not ensure complete male sterility of a female inbred plant. In this case, the resultant fertile female plants will successfully shed pollen and some female plants will be self-pollinated. This will result in seed of the female inbred being harvested along with the desired hybrid seed. Female inbred seed is not as productive as $F_1$ seed. In addition, the presence of female inbred seed can represent a germplasm security risk for the company producing the hybrid. The female inbred can also be mechanically detasseled. Mechanical detasseling is approximately as reliable as hand detasseling, but is faster and less costly. However, most detasseling machines produce more damage to the plants than hand detasseling, which reduces $F_1$ seed yields. Thus neither form of detasseling is presently entirely satisfactory, and a need continues to exist for alternative hybrid production methods that reduce production costs, increase production safety, and eliminate self-pollination of the female parent during the production of hybrid seed.

Another method of preventing parental plant selfing is to utilize parental plants that are male sterile or female sterile. Male fertility genes have been identified in a number of plants and include dominant and recessive male fertility genes. Plants that are homozygous for a recessive male fertility gene do not produce viable pollen and are useful as female parental plants. However, a result of the female plants being homozygous recessive for a male fertility gene is that they are not capable of selfing and, therefore, a means must be provided for obtaining pollen in order to maintain the parental P2 plant line. Generally, a maintainer cell line, which is heterozygous for the male fertility gene, is generated by crossing a homozygous dominant male fertile plant with the homozygous recessive female sterile plant. The heterozygous maintainer plants then are crossed with the homozygous recessive male sterile plants to produce a population in which 50% of the progeny are male sterile. The male sterile plants are then selected for use in generating hybrids. As such, the method requires additional breeding and selection steps to obtain the male sterile plants, thus adding to the time and cost required to produce the hybrid plants.

To overcome the requirement of having to select male sterile from male fertile plants generated by crossing a maintainer plant line with a female (male sterile) plant line, methods have been developed to obtain male sterile plants by expressing a cytotoxic molecule in cells of the male reproductive organs of a plant. For example, a nucleic acid encoding the cytotoxic molecule can be linked to a tapetum-specific promoter and introduced into plant cells, such that, upon expression, the toxic molecule kills anther cells, rendering the plant male sterile. As above, however, such female parental plants cannot be selfed and, therefore, require the preparation and use of a maintainer plant line, which, when crossed with the male sterile female parent restores fertility, for example, by providing a dominant male fertility gene, or by providing a means to inactivate or otherwise inhibit the activity of the cytotoxic gene product (see, U.S. Pat. No. 5,977,433).

Additional methods of conferring genetic male sterility have been described including, for example, generating plants with multiple mutant genes at separate locations within the genome that confer male sterility (see, U.S. Pat. Nos. 4,654,465 and 4,727,219) or with chromosomal translocations (see, U.S. Pat. Nos. 3,861,709 and 3,710,511). Another method of conferring genetic male sterility includes identifying a gene that is required for male fertility; silencing the endogenous gene, generating a transgene comprising an inducible promoter operably linked to the coding sequence of the male fertility gene, and inserting the transgene back into the plant, thus generating a plant that is male sterile in the absence of the inducing agent, and can be restored to male fertile by exposing the plant to the inducing agent (see, U.S. Pat. No. 5,432,068).

While the previously described methods of obtaining and maintaining hybrid plant lines have been useful for plant breeding and agricultural purposes, they require numerous steps and/or additional lines for maintaining male sterile or female sterile plant populations in order to obtain the hybrid plants. Such requirements contribute to increased costs for growing the hybrid plants and, consequently, increased costs to consumers. Thus, a need exists for convenient and effective methods of producing hybrid plants, and particularly for generating parental lines that can be crossed to obtain hybrid plants.

A reliable system of genetic male sterility would provide a number of advantages over other systems. The laborious detasseling process can be avoided in some genotypes by using cytoplasmic male-sterile (CMS) inbreds. In the absence of a fertility restorer gene, plants of a CMS inbred are male sterile as a result of cytoplasmic (non-nuclear) genome factors. Thus, this CMS characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile. Usually seed from detasseled normal maize and CMS-produced seed of the same hybrid must be blended to insure that adequate pollen loads are available for fertilization when the hybrid plants are grown and to insure cytoplasmic diversity.

Another type of genetic sterility is disclosed in U.S. Pat. Nos. 4,654,465 and 4,727,219 to Brar, et al. However, this form of genetic male sterility requires maintenance of multiple mutant genes at separate locations within the genome and requires a complex marker system to track the genes, making this system inconvenient. Patterson described a genetic system of chromosomal translocations, which can be effective, but is also very complex. (See, U.S. Pat. Nos. 3,861, 709 and 3,710,511).

Many other attempts have been made to address the drawbacks of existing sterility systems. For example, Fabijanski, et al., developed several methods of causing male sterility in plants (see, EPO 89/3010153.8 Publication Number 329,308 and PCT Application Number PCT/CA90/00037 published as WO 90/08828). One method includes delivering into the plant a gene encoding a cytotoxic substance that is expressed using a male tissue specific promoter. Another involves an antisense system in which a gene critical to fertility is identified and an antisense construct to the gene inserted in the plant. Mariani, et al. also shows several cytotoxic antisense systems. See, EP Number 89/401,194. Still other systems use "repressor" genes that inhibit the expression of other genes critical to male fertility. See, WO 90/08829.

A still further improvement of this system is one described at U.S. Pat. No. 5,478,369 in which a method of imparting controllable male sterility is achieved by silencing a gene native to the plant that is critical for male fertility and further introducing a functional copy of the male fertility gene under the control of an inducible promoter which controls expression of the gene. The plant is thus constitutively sterile, becoming fertile only when the promoter is induced, allowing for expression of the male fertility gene.

In a number of circumstances, a particular plant trait is expressed by maintenance of a homozygous recessive condition. Difficulties arise in maintaining the homozygous condition when a transgenic restoration gene must be used for maintenance. For example, the MS45 gene in maize (U.S. Pat. No. 5,478,369) has been shown to be critical to male fertility. Plants heterozygous or hemizygous for the dominant MS45 allele are fully fertile due to the sporophytic nature of the MS45 fertility trait. A natural mutation in the MS45 gene, designated ms45, imparts a male sterility phenotype to plants when this mutant allele is in the homozygous state. This sterility can be reversed (i.e., fertility restored) when the non-mutant form of the gene is introduced into the plant, either through normal crossing or transgenic complementation methods. However, restoration of fertility by crossing removes the desired homozygous recessive condition, and both methods restore full male fertility and prevent maintenance of pure male sterile maternal lines. The same concerns arise when controlling female fertility of the plant, where a homozygous recessive female must be maintained by crossing with a plant containing a restoration gene. Therefore there is considerable value not only in controlling the expression of restoration genes in a genetic recessive line, but also in controlling the transmission of the restoring genes to progeny during the hybrid production process.

SUMMARY OF THE INVENTION

The present invention is based on the determination that the genotype of an organism (e.g., a plant or mammal) can be modified to contain dominant suppressor alleles or transgene constructs that reduce, but not ablate, the activity of a gene, wherein the phenotype of the organism is not substantially affected. For example, plants can contain dominant suppressor alleles and/or transgene constructs that suppress the activity of a plant male fertility gene, without rendering the plant male sterile, or can contain dominant suppressor alleles and/or transgene constructs that suppress the activity of a gene required for viability, without killing the plant. Further, pairs of such plants having selected genotypes comprising the dominant suppressor alleles or transgene constructs can be crossed to produce progeny that exhibit the phenotypic change (e.g., male sterility). Progeny of plants comprising suppressed male fertility genes, for example, can be useful as females in hybrid plant production.

Accordingly, in one embodiment, the present invention relates to a breeding pair of plants, wherein the plants comprising the breeding pair are fertile (i.e., male fertile and female fertile), and wherein sterile progeny (e.g., male sterile progeny) are produced by crossing the breeding pair of plants. A breeding pair of plants of the invention can include, for example, a first plant having an inactivated first endogenous fertility gene, wherein the first plant is fertile; and a second plant having an inactivated second endogenous fertility gene, wherein the second plant is fertile. Such a breeding pair is further characterized in that, if the first endogenous fertility gene is a male fertility gene, then the second endogenous fertility gene also is a male fertility gene, and, similarly, if the first endogenous fertility gene is a female fertility gene, then the second endogenous fertility gene also is a female fertility gene.

In a breeding pair of plants of the invention, the first endogenous fertility gene and the second endogenous fertility gene can encode gene products that are present in a single pathway involved in determining fertility of a plant, or the first endogenous fertility gene and the second endogenous fertility gene can encode gene products that are in separate but convergent pathways. In either case, the presence of a single inactivated fertility gene in a plant does not substantially affect fertility of the plant, or plants derived therefrom, except that when a first and second plant as defined herein are crossed, the inactivation of both a first and a second fertility gene in progeny plants results in the progeny plants being sterile (i.e., male sterile or female sterile).

The inactivated fertility gene can be inactivated due, for example, to a mutation (e.g., deletion, substitution, or insertion of one or more nucleotides in the coding or non-coding sequence that reduces or inhibits expression of the fertility gene), including, for example, knock out of the gene (e.g., by a homologous recombination event), preferably in both alleles of the fertility gene. The inactivated fertility gene also can be inactivated due, for example, to expression of a gene product such as a transgene product (e.g., an RNA or an encoded polypeptide) in cells of the plant in which the gene normally is expressed, or in progenitor cells, wherein the gene product reduces or inhibits expression of the endogenous fertility gene. Further, in a breeding pair of plants of the invention, the first endogenous fertility gene of the first plant and the second endogenous fertility gene of the second plant can be inactivated in the same or different ways. For example, the first endogenous fertility gene can be inactivated due to a mutation, and the second endogenous fertility gene can be inactivated due to expression of a transgene product (e.g., a hairpin RNA comprising a nucleotide sequence of the promoter of the second fertility gene).

In various embodiments, the breeding pair can include a first plant, in which the first endogenous fertility gene is inactivated by a mutation, and a second plant having a second endogenous fertility gene inactivated in a manner other than a mutation; or can include a first plant in which the first endogenous fertility gene is inactivated by a mutation, and a second plant in which the second endogenous fertility gene is inactivated by a mutation; or can include a first plant having a first endogenous fertility gene inactivated in a manner other than a mutation, and a second plant in which the second endogenous fertility gene is inactivated in a manner other than by a mutation. In aspects of this embodiment, the first or second endogenous fertility gene of the first or second plant is inactivated by knockout of the first or second fertility gene, respectively; or the first or second endogenous fertility gene of the first or second plant is inactivated by mutation of the promoter of the first or second fertility gene, respectively. In further aspects, the first and second endogenous fertility genes of the first and second plants are inactivated by knockout of the first and second fertility genes, respectively; or the first and second endogenous fertility genes of the first and second plants are inactivated by mutation of the promoter of the first and second fertility genes, respectively.

In other embodiments, in a breeding pair of plants of the invention, the first endogenous fertility gene is inactivated due to expression in the first plant of a first exogenous nucleic acid molecule comprising a promoter operably linked to a nucleotide sequence encoding a first hairpin (hp) ribonucleic acid (RNA) molecule (hpRNA), wherein the first hpRNA comprises a nucleotide sequence of the first endogenous fertility gene promoter, and wherein, upon expression, the first hpRNA suppresses expression of the first endogenous fertility gene; or the second endogenous fertility gene is inactivated due to expression in the second plant of a second exogenous nucleic acid molecule comprising a promoter operably linked to a nucleotide sequence encoding a second hpRNA, wherein the second hpRNA comprises a nucleotide sequence of the second endogenous fertility gene promoter, and wherein, upon expression, the second hpRNA suppresses expression of the second endogenous fertility gene; or both the first endogenous fertility gene and second endogenous fertility gene are inactivated due to expression in the first plant and second plant of a first hpRNA and a second hpRNA, respectively, having the above-described characteristics. In aspects of this embodiment, the first exogenous nucleic acid molecule, when present, is stably integrated in the genome of cells of the first plant; or the second exogenous nucleic acid molecule, when present is stably integrated in the genome of cells of the second plant; or both the first exogenous nucleic acid molecule, when present, and the second exogenous nucleic acid molecule, when present, are stably integrated in the genome of cells of the first plant and second plant, respectively.

Where a first and/or second endogenous fertility gene is inactivated due to expression in a first and/or second plant, respectively, of an exogenous nucleic acid molecule comprising a promoter operably linked to a nucleotide sequence encoding an hpRNA, the promoter can be any promoter that is active in plant cells, for example, a constitutively active promoter, (e.g., an ubiquitin promoter), a tissue specific promoter, particularly a reproductive tissue promoter (e.g., an anther specific promoter such as a tapetum specific promoter), an inducible promoter, or a developmental or stage specific promoter. The fertility gene that is inactivated can be a male fertility gene or a female fertility gene, provided that, if a male fertility gene is inactivated in a first plant of a breeding pair (i.e., a first endogenous male fertility gene), the second plant of the breeding pair has an inactivated male fertility gene that is different from the first endogenous male fertility gene; and, conversely, if a female fertility gene is inactivated in a first plant of a breeding pair (i.e., a first endogenous female fertility gene), the second plant of the breeding pair has an inactivated female fertility gene that is different from the first endogenous female fertility gene. Further, the inactivation of a first or second endogenous fertility gene, alone, does not render a plant sterile, whereas a cross of a first plant having the first inactivated fertility gene and a second plant having the second inactivated fertility gene generates progeny that are sterile.

In another embodiment, the present invention relates to a breeding pair of transgenic plants, which includes a first fertile transgenic plant having integrated in its genome a first exogenous nucleic acid molecule comprising a promoter operably linked to a nucleotide sequence encoding a first hpRNA, wherein the first hpRNA comprises a nucleotide sequence from a first endogenous fertility gene promoter, and wherein, upon expression, the first hpRNA suppresses expression of the first endogenous fertility gene; and a second fertile transgenic plant having integrated in its genome a second exogenous nucleic acid molecule comprising a promoter operably linked to a nucleotide sequence encoding a second hpRNA, wherein the second hpRNA comprises a nucleotide sequence from a second endogenous fertility gene promoter, wherein the second endogenous fertility gene is different from the first endogenous fertility gene, and wherein, upon expression, the second hpRNA suppresses expression of the second endogenous fertility gene. As disclosed herein, the first endogenous gene is different from the second endogenous gene and, further if, in a breeding pair of plants, the first endogenous fertility gene of the first plant is a male fertility gene, then the second endogenous fertility gene of the second plant of the breeding pair also is a male fertility gene; whereas if the first endogenous fertility gene of the first plant is a female fertility gene, then the second endogenous fertility gene of the second plant also is a female fertility gene.

In certain embodiments, in an exogenous nucleic acid molecule contained in a first or second transgenic plant of a breeding pair of plants of the invention, the nucleotide sequence encoding the first or second hpRNA, respectively, is such that it includes the sequence of the promoter of the fertility gene that is to be inactivated, particularly an inverted repeat of the promoter sequence such that, upon expression, self-hybridization of the RNA results in formation of the hpRNA. As such, the nucleotide sequence, when expressed in a cell, forms a hairpin RNA molecule (i.e., an hpRNA), which suppresses (i.e., reduces or inhibits) expression of the endogenous fertility gene from its endogenous promoter.

The promoter, which is operably linked to the nucleotide sequence encoding the hpRNA in an exogenous nucleic acid molecule contained in a first or second transgenic plant of a breeding pair, can be any promoter that is active in plant cells, particularly a promoter that is active (or can be activated) in reproductive tissues of a plant (e.g., stamens or ovaries). As such, the promoter can be, for example, a constitutively active promoter, an inducible promoter, a tissue-specific promoter, or a developmental stage specific promoter. Also, the promoter of the first exogenous nucleic acid molecule can be the same as or different from the promoter of the second exogenous nucleic acid molecule.

In general, a promoter is selected based, for example, on whether endogenous fertility genes to be inhibited are male fertility genes or female fertility genes. Thus, where the endogenous genes to be inhibited are male fertility genes (e.g., a BS7 gene and an SB200 gene), the promoter can be a stamen specific and/or pollen specific promoter such as an MS45 gene promoter (U.S. Pat. No. 6,037,523), a 5126 gene promoter (U.S. Pat. No. 5,837,851), a BS7 gene promoter (WO 02/063021), an SB200 gene promoter (WO 02/26789), a TA29 gene promoter (*Nature* 347:737 (1990)), a PG47 gene promoter (U.S. Pat. No. 5,412,085; U.S. Pat. No. 5,545,546; *Plant J* 3(2):261-271 (1993)), an SGB6 gene promoter (U.S. Pat. No. 5,470,359) a G9 gene promoter (U.S. Pat. Nos. 5,837,850 and 5,589,610), or the like, such that the hpRNA is expressed in anther and/or pollen or in tissues that give rise to anther cells and/or pollen, thereby reducing or inhibiting expression of the endogenous male fertility genes (i.e., inactivating the endogenous male fertility genes). In comparison, where the endogenous genes to be inhibited are female fertility genes, the promoter can be an ovary specific promoter, for example. However, as disclosed herein, any promoter can be used that directs expression of the hpRNA in the reproductive tissue of interest, including, for example, a constitutively active promoter such as an ubiquitin promoter, which generally effects transcription in most or all plant cells.

The present invention also provides cells of a first plant or of a second plant or of both a first plant and a second plant of a breeding pair of plants of the invention. In addition, seeds of the first plant and/or second plant are provided, as are cuttings of the first and/or second plant.

The present invention further relates to a transgenic non-human organism that is homozygous recessive for a recessive genotype, wherein the transgenic organism contains an expressible first exogenous nucleic acid molecule comprising a first promoter operably linked to a polynucleotide encoding a restorer gene, the expression of which restores the phenotype that is otherwise absent due to the homozygous recessive genotype, and a second exogenous nucleic acid molecule encoding an hpRNA. The transgenic non-human organism can be any non-human organism that has a diploid (or greater) genome, including, for example, mammals, birds, reptiles, amphibians, or plants.

In one embodiment, the second expressible exogenous nucleic acid molecule of a transgenic plant of the invention encodes an hpRNA specific for the first promoter, which drives expression of the restorer gene. In one aspect of this embodiment, the second expressible exogenous nucleic acid molecule further comprises a second promoter operably linked to the nucleotide sequence encoding the hpRNA. The second promoter generally is different from the first promoter (of the first expressible exogenous nucleic acid molecule), and can be, for example, a constitutive promoter, an inducible promoter, a tissue specific promoter, or a developmental stage specific promoter, such that the hpRNA can be expressed in the transgenic organism in a constitutive manner, an inducible manner, a tissue specific manner, or at a particular stage of development. In another embodiment, the second expressible exogenous nucleic acid molecule of a transgenic plant of the invention encodes an hpRNA specific for a promoter other than the first promoter which drives expression of the restorer gene of the first expressible exogenous nucleic acid molecule.

A transgenic non-human organism of the invention is exemplified herein by a transgenic plant that is homozygous recessive for a recessive sterile genotype (e.g., homozygous recessive for the ms45 gene, which is a male fertility gene), and that contains (a) a first expressible transgene comprising a first promoter operably linked to a nucleotide sequence encoding a restorer gene, which, upon expression, restores fertility to the transgenic plant (e.g., transgene comprising an MS45 coding sequence), and (b) a second expressible transgene encoding an hpRNA, which, upon expression, suppresses expression by a second promoter, which is different from the first promoter. In one embodiment, the first promoter is a constitutive or developmentally regulated promoter, wherein the fertility restorer gene is expressed in the transgenic plant, and the transgenic plant is fertile. In another embodiment, the first promoter is an inducible promoter, wherein, upon contact of the transgenic plant with an appropriate inducing agent, expression of the fertility restorer gene is induced, rendering the transgenic plant fertile.

In another embodiment, the present invention also relates to a breeding pair of transgenic non-human organisms, including a first transgenic organism and second transgenic organism each of which is homozygous recessive for the same recessive genotype. The breeding pair is further characterized in that the first transgenic organism contains an expressible first exogenous nucleic acid molecule comprising a first promoter operably linked to a nucleotide sequence encoding a restorer gene, the expression of which restores the phenotype that is otherwise absent due to the homozygous recessive genotype, and a second expressible exogenous nucleic acid molecule that encodes an hpRNA specific for a second promoter, which is different from the first promoter. The second transgenic organism contains an expressible third exogenous nucleic acid molecule comprising the second promoter operably linked to a nucleotide sequence encoding a restorer gene, the expression of which restores the phenotype that is otherwise absent due to the homozygous recessive genotype, and a fourth expressible exogenous nucleic acid molecule that encodes an hpRNA specific for the first promoter. The first and second transgenic non-human organism are further characterized in that, when bred with each other, progeny are produced in which the second hpRNA inhibits expression of the restorer gene of the first transgene and the first hpRNA inhibits expression of the restorer gene of the third transgene, such that the progeny exhibit the recessive phenotype of the homozygous recessive genotype.

A breeding pair of transgenic non-human organisms of the invention is exemplified by a breeding pair of transgenic plants, as follows.

The first plant of the pair is a fertile transgenic plant having a homozygous recessive sterile genotype, having integrated in its genome a first exogenous nucleic acid molecule comprising a nucleotide sequence encoding a fertility restorer gene operably linked to a heterologous first promoter, wherein expression of the restorer gene restores fertility to the first transgenic plant; and a second exogenous nucleic acid molecule comprising a first hpRNA, wherein the first hpRNA comprises a nucleotide sequence of a second promoter, and wherein, upon expression, the first hpRNA suppresses expression from the second promoter, which is different from the first promoter.

The second transgenic plant of the pair has the same homozygous recessive sterile genotype as the first transgenic plant, and has integrated in its genome a third exogenous nucleic acid molecule, which comprises a nucleotide sequence encoding the fertility restorer gene operably linked to the second promoter, which is heterologous to the fertility restorer gene, wherein expression of the restorer gene restores fertility to the second transgenic plant; and a fourth exogenous nucleic acid molecule comprising a second hpRNA, wherein the second hpRNA comprises a nucleotide sequence of the heterologous first promoter, and wherein, upon expression, the second hpRNA suppresses expression of the first exogenous nucleic acid molecule comprising the heterologous first promoter.

As disclosed herein, in progeny of a cross of the first and second transgenic plants, the second hpRNA suppresses expression of the first exogenous nucleic acid molecule, including the fertility restorer gene contained therein, and the first hpRNA suppresses expression of the third exogenous nucleic acid molecule, including the fertility restorer gene contained therein. As such, the progeny are sterile, for example, female sterile. A breeding pair of transgenic plants of the invention can be homozygous recessive for male fertility genes (i.e., male sterile, except upon expression of the fertility restorer gene), or can be homozygous recessive for female fertility genes (i.e., female sterile, except upon expression of the fertility restorer gene).

In one aspect, a breeding pair of transgenic plants of the invention includes a first transgenic plant, which is homozygous recessive for ms45, wherein the first exogenous nucleic acid molecule comprises a nucleotide sequence encoding MS45 operably linked to a 5126 gene promoter, and the second exogenous nucleic acid molecule comprises a first hpRNA comprising an inverted repeat of a BS7 gene promoter. Said breeding pair further includes a second transgenic plant, which is homozygous recessive for ms45, wherein the third exogenous nucleic acid molecule comprises a nucleotide sequence encoding MS45 operably linked to the BS7 gene promoter, and the fourth exogenous nucleic acid molecule comprises a second hpRNA comprising an inverted repeat of the 5126 gene promoter. Upon crossing such first and second transgenic plants, male sterile progeny plants are obtained.

The present invention also relates to methods of producing a sterile plant. Such a method can be performed by crossing a breeding pair of plants as disclosed herein. In one embodiment, the first plant of the breeding pair contains a mutation inactivating a first endogenous gene of a pathway involved in male fertility, and the second plant contains a second endogenous gene of the same or a different but convergent pathway also involved in the male sterility, wherein the progeny plants are double mutants and have a male sterile phenotype. In another embodiment, the method is performed using first and second transgenic plants, each containing a transgene encoding an hpRNA that inactivates the respective endogenous fertility gene in the second and first transgenic plants, wherein progeny plants produced by crossing the parental plants exhibit the sterile phenotype.

The present invention also relates to a method of producing a transgenic non-human organism that exhibits a recessive phenotype, by breeding parental transgenic organisms that do not exhibit the recessive phenotype. For example, the invention provides methods of producing a sterile progeny plant by crossing first and second transgenic plants, each of which is homozygous recessive for the same fertility gene, wherein, in the first transgenic plant, a fertility restorer gene is expressed from a first promoter and an hpRNA is expressed that suppresses expression from a second promoter, and in the second transgenic plant, the fertility restorer gene is expressed from the second promoter, and a second hpRNA is expressed that suppresses expression of the first promoter. The sterile progeny plants can be female sterile or male sterile plants. For example, in a cross of a first transgenic plant containing a first exogenous nucleic acid molecule comprising a nucleotide sequence encoding MS45 operably linked to a 5126 gene promoter, and a second exogenous nucleic acid molecule comprising a first hpRNA including a nucleotide sequence of a BS7 gene promoter; and a second transgenic plant containing a third exogenous nucleic acid molecule comprising a nucleotide sequence encoding MS45 operably linked to the BS7 gene promoter, and a fourth exogenous nucleic acid molecule comprising a second hpRNA including a nucleotide sequence of the 5126 gene promoter, male sterile progeny are produced. Accordingly, the invention provides a plant produced by a method as disclosed herein, for example, a male sterile plant.

The present invention further relates to a method of producing hybrid plant seed. Such a method can be performed, for example, by pollinating (e.g., naturally, mechanically, or by hand) a male sterile plant produced as disclosed herein with pollen of a male fertile plant that contains at least one dominant allele corresponding to the homozygous recessive sterile genotype of the male sterile plant, whereby pollinated male sterile plants produce hybrid seed. As such, the invention also provides hybrid seed produced by such a method. The present invention relates to a method of obtaining a hybrid plant by growing such hybrid seed and, further, provides hybrid plants produced by growing such hybrid seed.

The present invention further relates to a method of identifying a function of a gene expressed in a cell. The gene expressed in the cell can be any gene containing a promoter, including an endogenous gene, which contains an endogenous promoter. A method of identifying a gene function can be performed, for example, by introducing into a cell in which the gene is expressed, a first exogenous nucleic acid molecule comprising a nucleotide sequence encoding a hpRNA operably linked to a first heterologous promoter, wherein the hpRNA comprises a nucleotide sequence of an endogenous promoter of the gene whose function is being examined, and wherein, upon expression, the hpRNA suppresses expression of the gene; and detecting a change in a phenotype of the cell upon expression of the hpRNA as compared to a wild type phenotype in the absence of expression of the hpRNA, whereby the change in phenotype identifies the function of the gene. In one aspect, the method further includes introducing into the cell a second exogenous nucleic acid molecule comprising a nucleotide sequence encoding a polypeptide encoded by the gene operably linked to a second heterologous promoter, wherein, upon expression of the polypeptide encoded by the gene from the second heterologous promoter, the wild type phenotype is restored.

A method of the invention can be practiced using single cells containing the gene of interest, or can be practiced using an organism containing the cell. The organism can be any organism of interest in which the gene of interest is expressed. In one embodiment, the cell is a plant cell, which can be a plant cell in vitro or can be one or more cells of a plant in situ. In one embodiment, the organism is a transgenic plant, which contains the first exogenous nucleic acid molecule stably integrated in its genome. In an aspect of this embodiment, the transgenic plant further contains, integrated in its genome, a second exogenous nucleic acid molecule (comprising a nucleotide sequence encoding a polypeptide encoded by the gene of interest) operably linked to a second heterologous promoter, wherein, upon expression of the second exogenous nucleic acid molecule from the second heterologous promoter, the wild type phenotype is restored.

In some embodiments, the present invention addresses the difficulty in propagating a plant having a homozygous recessive reproductive trait without losing the homozygous recessive condition in the resulting progeny. This may be accomplished by introducing into a plant at least one restoring transgene construct, operably linking (1) a first nucleotide sequence comprising a functional copy of a gene that complements the mutant phenotypic trait produced by the homozygous recessive condition with (2) a second functional nucleotide sequence which interferes with the formation, function, or dispersal of the male gametes of the plant and is operably linked to a male-gamete-tissue-preferred promoter. This construct is maintained in the hemizygous state and a plant containing such a construct is referred to herein as a maintainer. When the maintainer plant containing such a linked construct is used as a pollen donor to fertilize the homozygous recessive plant, the only viable male gametes provided to the homozygous recessive plant are those which contain the recessive allele, and do not contain any component of the transgene construct. None of the pollen grains which contain the restoring transgene construct are viable, due to the action of the linked second gene that prevents the formation of viable pollen. Therefore, the progeny resulting from such a sexual cross are non transgenic with respect to this transgene construct.

While no viable pollen produced by the maintainer contains the restoring transgene construct, 50% of the ovules (the female gamete) of the maintainer will contain the restoring transgene construct. Therefore, the maintainer can be propagated by self-fertilization, with the restoring transgene construct segregating such that it will be contained in 50% of the seed of the ear of a self fertilized maintainer. By linking the restoring transgene construct with a selectable marker, the 50% of the seed containing the transgene can be isolated to propagate the maintainer population, which remains homozygous for the recessive gene and hemizygous for the restoring transgene construct.

In a further embodiment, if the female gamete is prohibited from being formed or functional, it will be desirable to link the gene capable of complementing this mutant phenotype with an inducible promoter to aid in maintenance of the maintainer plant. Such a plant, when exposed to the inducing condition, will have female fertility restored, and the plant may then be self fertilized to produce progeny having the both the desired recessive mutant trait and the restoring transgene construct.

While the invention is exemplified in plants, a person of skill in the art would recognize its applicability to other non-human organisms, including mammals. For example, the invention encompasses a method of suppressing a phenotype in progeny of a parental pair of non-human organisms, wherein (a) said phenotype is expressed in each of said parents; (b) the genome of each parent is manipulated so as to inactivate a gene affecting the phenotype of interest; and (c) the gene inactivated in the first parent encodes a different gene product than the gene inactivated in the second parent.

DETAILED DESCRIPTION OF THE INVENTION

Embodiments of the invention reflect the determination that the genotype of an organism can be modified to contain dominant suppressor alleles or transgene constructs that suppress (i.e., reduce, but not ablate) the activity of a gene, wherein the phenotype of the organism is not substantially affected.

In some embodiments, the present invention is exemplified with respect to plant fertility, and more particularly with respect to plant male fertility. For example, plants may be genetically modified to contain a transgene construct encoding hairpin RNA (hpRNA) molecules that suppress the expression of an endogenous male fertility gene without rendering the plant male sterile.

In one example, Gene A and Gene B modulate sequential (though not necessarily consecutive) steps in a pathway leading to a product. In a first plant, Gene A is suppressed so as to reduce, but not ablate, Gene A activity. The pathway is not substantially inhibited, and thus the phenotype of said first plant is not affected. In a second plant, Gene B is suppressed so as to reduce, but not ablate, Gene B activity. The pathway is not substantially inhibited, and thus the phenotype of said second plant is not affected. In progeny of a cross of said first and second plants, the combination of suppression of Gene A and Gene B leads to loss of the product of the pathway and a change in phenotype. Suppression of Gene A and/or Gene B could be accomplished by use of hairpin constructs (hpRNA) as described elsewhere herein.

In another example, Gene A and Gene B modulate steps of convergent pathways prior to the point of convergence, and the converged pathway leads to a product. In a first plant, Gene A is suppressed so as to reduce, but not ablate, Gene A activity, and the phenotype of said first plant is not affected. In a second plant, Gene B is suppressed so as to reduce, but not ablate, Gene B activity, and the phenotype of said second plant is not affected. In progeny of a cross of said first and second plants, the combination of suppression of Gene A and Gene B leads to loss of the product of the convergent pathways. Suppression of Gene A and/or Gene B could be accomplished by use of hairpin constructs (hpRNA) as described elsewhere herein.

In certain embodiments, Gene A and Gene B modulate steps of pathways involved in plant fertility. In this way, for example, crosses of phenotypically fertile plants expressing targeted hpRNA molecules can generate male sterile plants. For example, parental plants having a homozygous recessive male sterile genotype can be transformed such that each expresses a restorer male fertility gene from different heterologous promoters and hpRNAs that suppress expression of the restorer gene in the other parental plant. Such parental plants, which are fertile, can be crossed with each other to generate male sterile plants. This is exemplified by a pair of male-fertile plants, A and B. Each has a homozygous recessive male sterile genotype, ms45 ms45. Plant A is transformed with, in single or multiple constructs, a 5126 promoter operably linked to a restorer MS45 gene, and an hpRNA specific for the BS7 promoter. Plant B is transformed with, in single or multiple constructs, a BS7 promoter operably linked to a restorer MS45 gene, and an hpRNA specific for the 5126 promoter. Plant A and Plant B are each male-fertile due to the presence of the MS45 restorer. In a cross of Plant A and Plant B, restoration of fertility is reversed due to the action of the complementing hairpin constructs targeted to the respective promoters driving the restorer gene, and the progeny of said cross are male-sterile. Such progeny are useful as females in hybrid production. Wild-type pollen can restore fertility in the hybrid due to the recessive nature of the ms45 allele.

Certain embodiments of the invention comprise a transgenic non-human organism having a homozygous recessive genotype that results in absence of a particular phenotype of interest, said organism further comprising (a) a first exogenous nucleic acid molecule comprising a restorer gene for the particular phenotype, operably linked to a first promoter; and (b) a second exogenous nucleic acid molecule comprising a second promoter operably linked to a nucleotide sequence encoding a first hairpin ribonucleic acid molecule (hpRNA), wherein the first hpRNA comprises a nucleotide sequence of the first promoter or a nucleotide sequence of a third promoter, wherein said transgenic non-human organism exhibits the phenotype of interest.

The agriculture industry produces crops that are used to feed humans and animals, and that are further used in other industries to prepare products as diverse as adhesives and explosives. Maize (corn), for example, is used as human food, livestock feed (e.g., beef cattle, dairy cattle, hogs, and poultry feed), and a raw material in industry. Food uses of maize include consumption of maize kernels as well as products of dry-milling and wet-milling industries (e.g., grits, meal, flour, maize starch, maize syrups, and dextrose). Maize oil is recovered from maize germ, which is a by-product of the dry-milling and wet-milling industries. Industrial uses of maize include production of ethanol, maize starch in the wet-milling industry and maize flour in the dry-milling industry. The industrial applications of maize starch and flour are based on their functional properties, including, for example, viscosity, film formation, adhesive properties, and ability to suspend particles. Maize starch and flour have application in the paper and textile industries, and also are used in adhesives, building materials, foundry binders, laundry starches, explosives, oil-well muds, and other mining applications.

Many crop plants, including rice, wheat, maize, tomatoes, and melons are grown as hybrids, which exhibit greater vigor and improved qualities as compared to the parental plants. The development of hybrids in a plant breeding program requires, in general, the development of homozygous inbred lines, the crossing of these lines, and the evaluation of the crosses. Pedigree breeding and recurrent selection breeding methods are used to develop inbred lines from breeding populations. For example, maize plant breeding programs combine the genetic backgrounds from two or more inbred lines (or various other germplasm sources) into breeding pools, from which new inbred lines are developed by self-pollinating (selfing) and selection of desired phenotypes. The selected inbreds then are crossed with other inbred lines and the hybrids from these crosses are evaluated to determine which of those have commercial potential. As such, plant breeding and hybrid development are expensive and time-consuming processes.

Pedigree breeding starts with the crossing of two genotypes, each of which may have one or more desirable characteristics that is lacking in the other or which complements the other. If the two original parents do not provide all the desired characteristics, other sources can be included in the breeding population. Using this method, superior plants are selected and selfed in successive generations until homogeneous plant lines are obtained. Recurrent selection breeding such as backcrossing can be used to improve an inbred line and a hybrid can be made using the inbreds. Backcrossing can be used to transfer a specific desirable trait from one inbred or source to a second inbred that lacks that trait, for example, by first crossing a superior inbred (recurrent parent) to a donor inbred (non-recurrent parent) that carries the appropriate gene (or genes) for the trait in question, crossing the progeny of the first cross back to the superior recurrent parent, and selecting in the resultant progeny for the desired trait to be transferred from the non-recurrent parent. After five or more backcross generations with selection for the desired trait, the progeny are homozygous for loci controlling the characteristic being transferred, and are like the superior parent for essentially all other genes. The last backcross generation is selfed to give pure breeding progeny for the gene being transferred.

A single cross hybrid (F1) results from the cross of two inbred lines (P1 and P2), each of which has a genotype that complements the genotype of the other. In the development of commercial hybrids in a maize plant breeding program, for example, only F1 hybrid plants are sought, as they are more vigorous than their inbred parents. This hybrid vigor (heterosis) can be manifested in many polygenic traits such as increased vegetative growth and increased yield. The development of a hybrid in a maize plant breeding program, for example, involves the selection of plants from various germplasm pools for initial breeding crosses; the selfing of the selected plants from the breeding crosses for several generations to produce a series of inbred lines, which, although different from each other, breed true and are highly uniform; and crossing the selected inbred lines with different inbred lines to produce the hybrid F1 progeny. During the inbreeding process in maize, the vigor of the lines decreases, but is restored when two different inbred lines are crossed to produce the hybrid plants. An important consequence of the homozygosity and homogeneity of the inbred lines is that the F1 hybrid between a defined pair of inbred parental plants always is the same. As such, once the inbreds that provide a superior hybrid are identified, the hybrid seed can be reproduced indefinitely as long as the inbred parents are maintained.

Hybrid seed production requires elimination or inactivation of pollen produced by the female parent. Incomplete removal or inactivation of the pollen provides the potential for selfing, raising the risk that inadvertently self-pollinated seed will unintentionally be harvested and packaged with hybrid seed. Once the seed is planted, the selfed plants can be identified and selected; the selfed plants are genetically equivalent to the female inbred line used to produce the hybrid. Typically, the selfed plants are identified and selected based on their decreased vigor. For example, female selfed plants of maize are identified by their less vigorous appearance for vegetative and/or reproductive characteristics, including shorter plant height, small ear size, ear and kernel shape, cob color, or other characteristics. Selfed lines also can be identified using molecular marker analyses (see, e.g., Smith and Wych, (1995) *Seed Sci. Technol.* 14:1-8). Using such methods, the homozygosity of the self-pollinated line can be verified by analyzing allelic composition at various loci in the genome.

Because hybrid plants are important and valuable field crops, plant breeders are continually working to develop high-yielding hybrids that are agronomically sound based on stable inbred lines. The availability of such hybrids allows a maximum amount of crop to be produced with the inputs used, while minimizing susceptibility to pests and environmental stresses. To accomplish this goal, the plant breeder must develop superior inbred parental lines for producing hybrids by identifying and selecting genetically unique individuals that occur in a segregating population. The present invention contributes to this goal, for example by providing plants that, when crossed, generate male sterile progeny, which can be used as female parental plants for generating hybrid plants.

A large number of genes have been identified as being tassel preferred in their expression pattern using traditional methods and more recent high-throughput methods. The correlation of function of these genes with important biochemical or developmental processes that ultimately lead to fertile pollen is arduous when approaches are limited to classical forward or reverse genetic mutational analysis. As disclosed herein, suppression approaches in maize provide an alternative rapid means to identify genes that are directly related to pollen development in maize. The well-characterized maize male fertility gene, MS45, and several anther-preferred genes of unknown function were used to evaluate the efficacy of generating male sterility using post-transcriptional gene silencing (PTGS; see, for example, Kooter, et al., (1999) *Trends Plant Sci.* 4:340-346) or transcriptional gene silencing (TGS; see, for example, Mette, et al., (2000) *EMBO J* 19:5194-5201) approaches.

To examine PTGS, hairpin-containing RNAi constructs that have stem structures composed of inverted repeats of the anther-expressed cDNA sequences, and a loop containing either a non-homologous coding sequence or a splicable intron from maize, were introduced into maize.

To examine TGS as an approach to knock out anther gene function, a second set of constructs was generated in which the promoters of the anther-specific gene sequences formed the stem and a non-homologous sequence formed the loop. The constructs were expressed using constitutive promoters and anther-preferred promoters.

Contrasting fertility phenotypes were observed, depending on the type of hairpin construct expressed. Plants expressing the PTGS constructs were male fertile. In contrast, plants expressing the TGS constructs were male sterile, and lacked MS45 mRNA and protein. Further, the sterility phenotype of the plants containing the hpRNA specific for the MS45 promoter (i.e., the TGS constructs) was reversed when MS45 was expressed from heterologous promoters in these plants. These results demonstrate that TGS provides a tool for rapidly correlating gene expression with function of unknown genes such as anther-expressed monocot genes.

Accordingly, the invention provides breeding pairs of plants, wherein the plants comprising the breeding pair are fertile (i.e., male fertile and female fertile), and wherein progeny produced by crossing the breeding pair of plants are sterile (e.g., male sterile). As disclosed herein, a breeding pair of plants of the invention can include, for example, a first plant having an inactivated first endogenous fertility gene, wherein the first plant is fertile; and a second plant having an inactivated second endogenous fertility gene, wherein the second plant is fertile. Such a breeding pair is characterized, in part, in that if the first endogenous fertility gene is a male fertility gene, then the second endogenous fertility gene also is a male fertility gene; whereas if the first endogenous fertility gene is a female fertility gene, then the second endogenous fertility gene also is a female fertility gene.

As used herein, the term "endogenous", when used in reference to a gene, means a gene that is normally present in the genome of cells of a specified organism, and is present in its normal state in the cells (i.e., present in the genome in the state in which it normally is present in nature). The term "exogenous" is used herein to refer to any material that is introduced into a cell. The term "exogenous nucleic acid molecule" or "transgene" refers to any nucleic acid molecule that either is not normally present in a cell genome or is introduced into a cell. Such exogenous nucleic acid molecules generally are recombinant nucleic acid molecules, which are generated using recombinant DNA methods as disclosed herein or otherwise known in the art. In various embodiments, a transgenic non-human organism as disclosed herein, can contain, for example, a first transgene and a second transgene. Such first and second transgenes can be introduced into a cell, for example, a progenitor cell of a transgenic organism, either as individual nucleic acid molecules or as a single unit (e.g., contained in different vectors or contained in a single vector, respectively). In either case, confirmation may be made that a cell from which the transgenic organism is to be derived contains both of the transgenes using routine and well-known methods such as expression of marker genes or nucleic acid hybridization or PCR analysis. Alternatively, or additionally, confirmation of the presence of transgenes may occur later, for example, after regeneration of a plant from a putatively transformed cell.

An endogenous fertility gene of a plant of a breeding pair of the invention can be inactivated due, for example, (1) to a mutation of the endogenous gene such that the function of a product encoded by the gene is suppressed (e.g., the gene product is not expressed or is expressed at a level that is insufficient to mediate its full effect in the plant or plant cell); or (2) to expression of an exogenous nucleic acid molecule that reduces or inhibits expression of the gene product encoded by the endogenous gene. As such, the term "inactivated" is used broadly herein to refer to any manipulation of an endogenous gene, or a cell containing the gene, such that the function mediated by a product encoded by the gene is suppressed. It should further be recognized that, regardless of whether the inactivated endogenous gene has reduced activity or is completely inactive, the desired relevant phenotype is maintained. As such, reference to an inactivated male fertility gene in a parental plant defined as having a male fertile phenotype can include, for example, a male fertility gene that is expressed at a level that is lower than normal, but sufficient to maintain fertility of the parental plant, or a male fertility gene that is completely inactive, and wherein fertility of the parental plant is maintained due to expression of a second gene product.

Mutation of an endogenous gene that results in suppression of the gene function can be effected, for example, by deleting or inserting one or a few nucleotides into the nucleotide sequence of the gene (e.g., into the promoter, coding sequence, or intron), by substituting one or a few nucleotides in the gene with other different nucleotides, or by knocking out the gene (e.g., by homologous recombination using an appropriate targeting vector). Plants having such mutations in both alleles can be obtained, for example, using crossing methods as disclosed herein or otherwise known in the art. Inactivation of an endogenous gene that results in suppression of the gene function also can be effected by introduction into cells of the plant of a transgene that suppresses expression of the endogenous gene or a product expressed from the endogenous gene (e.g., an encoded polypeptide), or a transgene that encodes a product (e.g., an RNA) that suppresses expression of the endogenous gene or a product encoded by the endogenous gene in cells of the plant in which the gene normally is expressed.

By way of example, inactivation of endogenous fertility genes can be effected by expressing hairpin RNA molecules (hpRNA) in cells of the reproductive organs of a plant (e.g., stamen cells where the endogenous fertility genes to be inactivated are male fertility genes). The stamen, which comprises the male reproductive organ of plants, includes various cell types, including, for example, the filament, anther, tapetum, and pollen. The hpRNAs useful for purposes of the present invention are designed to include inverted repeats of a promoter of the endogenous gene to be inactivated; hpRNAs having the ability to suppress expression of a gene have been described (see, e.g., Matzke, et al., (2001) *Curr. Opin. Genet. Devel.* 11:221-227; Scheid, et al., (2002) *Proc. Natl. Acad. Sci.*, USA 99:13659-13662; Waterhouse and Helliwell (2003) *Nature Reviews Genetics* 4:29-38; Aufsaftz, et al., (2002) *Proc. Nat'l. Acad. Sci.* 99(4):16499-16506; Sijen, et al., (2001) *Curr. Biol.* 11:436-440). As disclosed herein, the use of stamen-specific or stamen-preferred promoters, including anther-specific promoters, pollen-specific promoters, tapetum-specific promoters, and the like, allows for expression of hpRNAs in plants (particularly in male reproductive cells of the plant), wherein the hpRNA suppresses expression of an endogenous fertility gene, thereby inactivating expression of the endogenous fertility gene. As such, suppression using an hpRNA specific for a promoter that directs expression of a fertility gene provides a means to inactivate an endogenous fertility gene.

In one embodiment, a breeding pair of plants of the invention can include a first plant, which contains a first exogenous nucleic acid molecule comprising a promoter operably linked to a nucleotide sequence encoding a first hpRNA, wherein the first hpRNA comprises a nucleotide sequence comprising an inverted repeat of the first endogenous fertility gene promoter, and wherein, upon expression, the first hpRNA suppresses expression of the first endogenous fertility gene; and a second plant, which contains a second exogenous nucleic acid molecule comprising a promoter operably linked to a nucleotide sequence encoding a second hpRNA, wherein the second hpRNA comprises a nucleotide sequence comprising an inverted repeat of the second endogenous fertility gene promoter, and wherein, upon expression, the second hpRNA suppresses expression of the second endogenous fertility gene. According to the present invention, the first and/or second exogenous nucleic acid can, but need not, be stably integrated in the genome of cells of the first and/or second plant, respectively. Such first and second plants of the breeding pair are characterized, in part, in that each is fertile, and is further characterized in that, when crossed, the progeny of such cross is sterile (e.g., male sterile).

The terms "first", "second", "third", and "fourth" are used herein only to clarify relationships of various cells and molecules or to distinguish different types of a molecule, and, unless specifically indicated otherwise, are not intended to indicate any particular order, importance, or quantitative feature. For example, and unless specifically indicated otherwise, reference to a "first" plant containing a "first endogenous gene" is intended to indicate only that the specified gene is present in the specified plant. By way of a second example, and unless specifically indicated otherwise, reference to a "first plant containing a first transgene and a second transgene" is intended to indicate only that said plant contains two exogenous nucleic acid molecules that are different from each other.

As used herein, the term "nucleic acid molecule" or "polynucleotide" or "nucleotide sequence" refers broadly to a sequence of two or more deoxyribonucleotides or ribonucleotides that are linked together by a phosphodiester bond. As such, the terms include RNA and DNA, which can be a gene or a portion thereof, a cDNA, a synthetic polydeoxyribonucleic acid sequence, or the like, and can be single-stranded or double-stranded, as well as a DNA/RNA hybrid. Furthermore, the terms are used herein to include naturally-occurring nucleic acid molecules, which can be isolated from a cell, as well as synthetic molecules, which can be prepared, for example, by methods of chemical synthesis or by enzymatic methods such as by the polymerase chain reaction (PCR). The term "recombinant" is used herein to refer to a nucleic acid molecule that is manipulated outside of a cell, including two or more linked heterologous nucleotide sequences. The term "heterologous" is used herein to refer to nucleotide sequence that are not normally linked in nature or, if linked, are linked in a different manner than that disclosed. For example, reference to a transgene comprising a coding sequence operably linked to a heterologous promoter means that the promoter is one that does not normally direct expression of the nucleotide sequence in a specified cell in nature.

In general, the nucleotides comprising an exogenous nucleic acid molecule (transgene) are naturally occurring deoxyribonucleotides, such as adenine, cytosine, guanine or thymine linked to 2'-deoxyribose, or ribonucleotides such as adenine, cytosine, guanine or uracil linked to ribose. However, a nucleic acid molecule or nucleotide sequence also can contain nucleotide analogs, including non-naturally-occurring synthetic nucleotides or modified naturally-occurring nucleotides. Such nucleotide analogs are well known in the art and commercially available, as are polynucleotides containing such nucleotide analogs (Lin, et al., (1994) *Nucl. Acids Res.* 22:5220-5234; Jellinek, et al., (1995) *Biochemistry* 34:11363-11372; Pagratis, et al., (1997) *Nature Biotechnol.* 15:68-73). Similarly, the covalent bond linking the nucleotides of a nucleotide sequence generally is a phosphodiester bond, but also can be, for example, a thiodiester bond, a phosphorothioate bond, a peptide-like bond or any other bond known to those in the art as useful for linking nucleotides to produce synthetic polynucleotides (see, for example, Tam, et al., (1994) *Nucl. Acids Res.* 22:977-986; Ecker and Crooke, (1995) *BioTechnology* 13:351360). The incorporation of non-naturally occurring nucleotide analogs or bonds linking the nucleotides or analogs can be particularly useful where the nucleic acid molecule is to be exposed to an environment that can contain a nucleolytic activity, including, for example, a plant tissue culture medium or in a plant cell, since the modified molecules can be less susceptible to degradation.

A nucleotide sequence containing naturally-occurring nucleotides and phosphodiester bonds can be chemically synthesized or can be produced using recombinant DNA methods, using an appropriate polynucleotide as a template. In comparison, a nucleotide sequence containing nucleotide analogs or covalent bonds other than phosphodiester bonds generally is chemically synthesized, although an enzyme such as T7 polymerase can incorporate certain types of nucleotide analogs into a polynucleotide and, therefore, can be used to produce such a polynucleotide recombinantly from an appropriate template (Jellinek, et al., supra, 1995).

An exogenous nucleic acid molecule can comprise operably linked nucleotide sequences such as a promoter operably linked to a nucleotide sequence encoding an hpRNA, or a promoter linked to a nucleotide sequence encoding a male fertility gene product. The term "operably linked" is used herein to refer to two or more molecules that, when joined together, generate a molecule that shares features characteristic of each of the individual molecules. For example, when used in reference to a promoter (or other regulatory element) and a second nucleotide sequence encoding a gene product, the term "operably linked" means that the regulatory element is positioned with respect to the second nucleotide sequence such that transcription or translation of the isolated nucleotide sequence is under the influence of the regulatory element. When used in reference to a fusion protein comprising a first polypeptide and one or more additional polypeptides, the term "operably linked" means that each polypeptide component of the fusion (chimeric) protein exhibits some or all of a function that is characteristic of the polypeptide component (e.g., a cell compartment localization domain and a enzymatic activity). In another example, two operably linked nucleotide sequences, each of which encodes a polypeptide, can be such that the coding sequences are in frame and, therefore, upon transcription and translation, result in production of two polypeptides, which can be two separate polypeptides or a fusion protein.

Where an exogenous nucleic acid molecule includes a promoter operably linked to a nucleotide sequence encoding an RNA or polypeptide of interest, the exogenous nucleic acid molecule can be referred to as an expressible exogenous nucleic acid molecule (or transgene). The term "expressible" is used herein because, while such a nucleotide sequence can be expressed from the promoter, it need not necessarily actually be expressed at a particular point in time. For example, where a promoter of an expressible transgene is an inducible promoter lacking basal activity, an operably linked nucleotide sequence encoding an RNA or polypeptide of interest is expressed only following exposure to an appropriate inducing agent.

Transcriptional promoters generally act in a position- and orientation-dependent manner, and usually are positioned at or within about five nucleotides to about fifty nucleotides 5' (upstream) of the start site of transcription of a gene in nature. In comparison, enhancers can act in a relatively position- or orientation-independent manner, and can be positioned several hundred or thousand nucleotides upstream or downstream from a transcription start site, or in an intron within the coding region of a gene, yet still be operably linked to the coding region so as to enhance transcription. The relative positions and orientations of various regulatory elements in addition to a promoter, including the positioning of a transcribed regulatory sequence such as an internal ribosome entry site, or a translated regulatory element such as a cell compartmentalization domain in an appropriate reading frame, are well known, and methods for operably linking such elements are routine in the art (see, for example, Sambrook, et al., "Molecular Cloning: A laboratory manual" (Cold Spring Harbor Laboratory Press 1989); Ausubel, et al., "Current Protocols in Molecular Biology" (John Wiley and Sons, Baltimore Md. 1987, and supplements through 1995)).

Promoters useful for expressing a nucleic acid molecule of interest can be any of a range of naturally-occurring promoters known to be operative in plants or animals, as desired. Promoters that direct expression in cells of male or female reproductive organs of a plant are useful for generating a transgenic plant or breeding pair of plants of the invention. The promoters useful in the present invention can include constitutive promoters, which generally are active in most or all tissues of a plant; inducible promoters, which generally are inactive or exhibit a low basal level of expression, and can be induced to a relatively high activity upon contact of cells with an appropriate inducing agent; tissue-specific (or tissue-preferred) promoters, which generally are expressed in only one or a few particular cell types (e.g., plant anther cells); and developmental- or stage-specific promoters, which are active only during a defined period during the growth or development of a plant. Often promoters can be modified, if necessary, to vary the expression level. Certain embodiments comprise promoters exogenous to the species being manipulated. For example, the Ms45 gene introduced into ms45 ms45 maize germplasm may be driven by a promoter isolated from another plant species; a hairpin construct may then be designed to target the exogenous plant promoter, reducing the possibility of hairpin interaction with non-target, endogenous maize promoters.

Exemplary constitutive promoters include the 35S cauliflower mosaic virus (CaMV) promoter promoter (Odell, et al., (1985) *Nature* 313:810-812), the maize ubiquitin promoter (Christensen, et al., (1989) *Plant Mol. Biol.* 12:619-632 and Christensen, et al., (1992) *Plant Mol. Biol.* 18:675-689); the core promoter of the Rsyn7 promoter and other constitutive promoters disclosed in WO 99/43838 and U.S. Pat. No. 6,072,050; rice actin (McElroy, et al., (1990) *Plant Cell* 2:163-171); pEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026); rice actin promoter (U.S. Pat. No. 5,641,876; WO 00/70067), maize histone promoter (Brignon, et al., (1993) *Plant Mol Bio* 22(6): 1007-1015; Rasco-Gaunt, et al., (2003) *Plant Cell Rep.* 21 (6):569-576) and the like. Other constitutive promoters include, for example, those described in U.S. Pat. Nos. 5,608, 144 and 6,177,611, and PCT publication WO 03/102198.

Tissue-specific, tissue-preferred, or stage-specific regulatory elements further include, for example, the AGL8/FRUITFULL regulatory element, which is activated upon floral induction (Hempel, et al., (1997) *Development* 124:3845-3853); root-specific regulatory elements such as the regulatory elements from the RCP1 gene and the LRP1 gene (Tsugeki and Fedoroff, (1999) *Proc. Natl. Acad., USA* 96:12941-12946; Smith and Fedoroff, (1995) *Plant Cell* 7:735-745); flower-specific regulatory elements such as the regulatory elements from the LEAFY gene and the APETALA1 gene (Blazquez, et al., (1997) *Development* 124:3835-3844; Hempel, et al., supra, 1997); seed-specific regulatory elements such as the regulatory element from the oleosin gene (Plant, et al., (1994) *Plant Mol. Biol.* 25:193-205), and dehiscence zone specific regulatory element. Additional tissue-specific or stage-specific regulatory elements include the Zn13 promoter, which is a pollen-specific promoter (Hamilton, et al., (1992) *Plant Mol. Biol.* 18:211-218); the UNUSUAL FLORAL ORGANS (UFO) promoter, which is active in apical shoot meristem; the promoter active in shoot meristems (Atanassova, et al., (1992) *Plant J.* 2:291), the cdc2 promoter and cyc07 promoter (see, for example, Ito, et al., (1994) *Plant Mol. Biol.* 24:863-878; Martinez, et al., (1992) *Proc. Natl. Acad. Sci., USA* 89:7360); the meristematic-preferred meri-5 and H3 promoters (Medford, et al., (1991) *Plant Cell* 3:359; Terada, et al., (1993) *Plant J.* 3:241); meristematic and phloem-preferred promoters of Myb-related genes in barley (Wissenbach, et al., (1993) *Plant J.* 4:411); *Arabidopsis* cyc3aAt and cyc1At (Shaul, et al., (1996) *Proc. Natl. Acad. Sci.* 93:4868-4872); *C. roseus* cyclins CYS and CYM (Ito, et al., (1997) *Plant J.* 11:983-992); and *Nicotiana* CyclinB1 (Trehin, et al., (1997) *Plant Mol. Biol.* 35:667-672); the promoter of the APETALA3 gene, which is active in floral meristems (Jack, et al., (1994) *Cell* 76:703; Hempel, et al., supra, 1997); a promoter of an agamous-like (AGL) family member, for example, AGL8, which is active in shoot meristem upon the transition to flowering (Hempel, et al., supra, 1997); floral abscission zone promoters; L1-specific promoters; the ripening-enhanced tomato polygalacturonase promoter (Nicholass, et al., (1995) *Plant Mol. Biol.* 28:423-435), the E8 promoter (Deikman, et al., (1992) *Plant Physiol.* 100:2013-2017), and the fruit-specific 2A1 promoter, U2 and U5 snRNA promoters from maize, the Z4 promoter from a gene encoding the Z4 22 kD zein protein, the Z10 promoter from a gene encoding a 10 kD zein protein, a Z27 promoter from a gene encoding a 27 kD zein protein, the A20 promoter from the gene encoding a 19 kD zein protein, and the like. Additional tissue-specific promoters can be isolated using well known methods (see, e.g., U.S. Pat. No. 5,589,379). Shoot-preferred promoters include shoot meristem-preferred promoters such as promoters disclosed in Weigel, et al., (1992) *Cell* 69:843-859 (Accession Number M91208); Accession Number AJ131822; Accession Number Z71981; Accession Number AF049870 and shoot-preferred promoters disclosed in McAvoy, et al., (2003) *Acta Hort. (ISHS)* 625:379-385. Inflorescence-preferred promoters include the promoter of chalcone synthase (Van der Meer, et al., (1992) *Plant J.* 2(4):525-535), anther-specific LAT52 (Twell, et al., (1989) *Mol. Gen. Genet.* 217:240-245), pollen-specific Bp4 (Albani, et al., (1990) *Plant Mol Biol.* 15:605, maize pollen-specific gene Zm13 (Hamilton, et al., (1992) *Plant Mol. Biol.* 18:211-218; Guerrero, et al., (1993) *Mol. Gen. Genet.* 224:161-168), microspore-specific promoters such as the apg gene promoter (Twell, et al., (1993) *Sex. Plant Reprod.* 6:217-224), and tapetum-specific promoters such as the TA29 gene promoter (Mariani, et al., (1990) *Nature* 347:737; U.S. Pat. No. 6,372,967), and other stamen-specific promoters such as the MS45 gene promoter, 5126 gene promoter, BS7 gene promoter, PG47 gene promoter (U.S. Pat. No. 5,412,085; U.S. Pat. No. 5,545,546; *Plant J* 3(2):261-271 (1993)), SGB6 gene promoter (U.S. Pat. No. 5,470,359), G9 gene promoter (U.S. Pat. Nos. 5,8937,850; 5,589,610), SB200 gene promoter (WO 02/26789), or the like (see, Example 1). Tissue-preferred promoters of interest further include a sunflower pollen-expressed gene SF3 (Baltz, et al., (1992) *The Plant Journal* 2:713-721), *B. napus* pollen specific genes (Arnoldo, et al., (1992) *J. Cell. Biochem*, Abstract Number Y101204). Tissue-preferred promoters further include those reported by Yamamoto, et al., (1997) *Plant J.* 12(2):255-265 (psaDb); Kawamata, et al., (1997) *Plant Cell Physiol.* 38(7):792-803 (PsPAL1); Hansen, et al., (1997) *Mol. Gen Genet.* 254(3):337-343 (ORF13); Russell, et al., (1997) *Transgenic Res.* 6(2):157-168 (waxy or ZmGBS; 27 kDa zein, ZmZ27; osAGP; osGT1); Rinehart, et al., (1996) *Plant Physiol.* 112(3):1331-1341 (Fbl2A from cotton); Van Camp, et al., (1996) *Plant Physiol.* 112(2):525-535 (*Nicotiana* SodA1 and SodA2); Canevascini, et al., (1996) *Plant Physiol.* 112(2):513-524 (*Nicotiana* Itp1); Yamamoto, et al., (1994) *Plant Cell Physiol.* 35(5):773-778 (*Pinus* cab-6 promoter); Lam (1994) *Results Probl. Cell Differ.* 20:181-196; Orozco, et al., (1993) *Plant Mol Biol.* 23(6):1129-1138 (spinach rubisco activase (Rca)); Matsuoka, et al., (1993) *Proc Natl. Acad. Sci. USA* 90(20):9586-9590 (PPDK promoter); and Guevara-Garcia, et al., (1993) *Plant J.* 4(3):495-505 (*Agrobacterium* pmas promoter). A tissue-specific promoter that is active in cells of male or female reproductive organs can be particularly useful in certain aspects of the present invention.

"Seed-preferred" promoters include both "seed-specific" promoters (those promoters active during seed development such as promoters of seed storage proteins) as well as "seed-germinating" promoters (those promoters active during seed germination). See, Thompson, et al., (1989) *BioEssays* 10:108. Such seed-preferred promoters include, but are not limited to, Cim1 (cytokinin-induced message), cZ19B1 (maize 19 kDa zein), milps (myo-inositol-1-phosphate synthase); see, WO 00/11177 and U.S. Pat. No. 6,225,529. Gamma-zein is an endosperm-specific promoter. Globulin-1 (Glob-1) is a representative embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, gamma-zein, waxy, shrunken 1, shrunken 2, globulin 1, etc. See also, WO 00/12733 and U.S. Pat. No. 6,528,704, where seed-preferred promoters from end1 and end2 genes are disclosed. Additional embryo specific promoters are disclosed in Sato, et al., (1996) *Proc. Natl. Acad. Sci.* 93:8117-8122 (rice homeobox, OSH1); and Postma-Haarsma, et al., (1999) *Plant Mol. Biol.* 39:257-71 (rice KNOX genes). Additional endosperm specific promoters are disclosed in Albani, et al., (1984) *EMBO* 3:1405-15; Albani, et al., (1999) *Theor. Appl. Gen.* 98:1253-62; Albani, et al., (1993) *Plant J.* 4:343-55; Mena, et al., (1998) *The Plant Journal* 116:53-62 (barley DOF); Opsahl-Ferstad, et al., (1997) *Plant J* 12:235-46 (maize Esr); and Wu, et al., (1998) *Plant Cell Physiology* 39:885-889 (rice GluA-3, GluB-1, NRP33, RAG-1).

An inducible regulatory element is one that is capable of directly or indirectly activating transcription of one or more DNA sequences or genes in response to an inducer. The inducer can be a chemical agent such as a protein, metabolite, growth regulator, herbicide or phenolic compound; or a physiological stress, such as that imposed directly by heat, cold, salt, or toxic elements, or indirectly through the action of a pathogen or disease agent such as a virus; or other biological or physical agent or environmental condition. A plant cell containing an inducible regulatory element may be exposed to an inducer by externally applying the inducer to the cell or plant such as by spraying, watering, heating or similar methods. An inducing agent useful for inducing expression from an inducible promoter is selected based on the particular inducible regulatory element. In response to exposure to an inducing agent, transcription from the inducible regulatory element generally is initiated de novo or is increased above a basal or constitutive level of expression. Typically the protein factor that binds specifically to an inducible regulatory element to activate transcription is present in an inactive form which is then directly or indirectly converted to the active form by the inducer. Any inducible promoter can be used in the instant invention (see, Ward, et al., (1993) *Plant Mol. Biol.* 22:361-366).

Examples of inducible regulatory elements include a metallothionein regulatory element, a copper-inducible regulatory element, or a tetracycline-inducible regulatory element, the transcription from which can be effected in response to divalent metal ions, copper or tetracycline, respectively (Furst, et al., (1988) *Cell* 55:705-717; Mett, et al., (1993) *Proc. Natl. Acad. Sci.*, USA 90:4567-4571; Gatz, et al., (1992) *Plant J.* 2:397-404; Roder, et al., (1994) *Mol. Gen. Genet.* 243:32-38). Inducible regulatory elements also include an ecdysone regulatory element or a glucocorticoid regulatory element, the transcription from which can be effected in response to ecdysone or other steroid (Christopherson, et al., (1992) *Proc. Natl. Acad. Sci.*, USA 89:6314-6318; Schena, et al., (1991) *Proc. Natl. Acad. Sci.*, USA 88:10421-10425; U.S. Pat. No. 6,504,082); a cold responsive regulatory element or a heat shock regulatory element, the transcription of which can be effected in response to exposure to cold or heat, respectively (Takahashi, et al., (1992) *Plant Physiol.* 99:383-390); the promoter of the alcohol dehydrogenase gene (Gerlach, et al., (1982) *PNAS USA* 79:2981-2985; Walker, et al., (1987) *PNAS* 84(19):6624-6628), inducible by anaerobic conditions; and the light-inducible promoter derived from the pea rbcS gene or pea psaDb gene (Yamamoto, et al., (1997) *Plant J.* 12(2):255-265); a light-inducible regulatory element (Feinbaum, et al., (1991) *Mol. Gen. Genet.* 226:449; Lam and Chua, (1990) *Science* 248:471; Matsuoka, et al., (1993) *Proc. Natl. Acad. Sci. USA* 90(20):9586-9590; Orozco, et al., (1993) *Plant Mol. Bio.* 23(6):1129-1138), a plant hormone inducible regulatory element (Yamaguchi-Shinozaki, et al., (1990) *Plant Mol. Biol.* 15:905; Kares, et al., (1990) *Plant Mol. Biol.* 15:225), and the like. An inducible regulatory element also can be the promoter of the maize In2-1 or In2-2 gene, which responds to benzenesulfonamide herbicide safeners (Hershey, et al., (1991) *Mol. Gen. Gene.* 227:229-237; Gatz, et al., (1994) *Mol. Gen. Genet.* 243:32-38), and the Tet repressor of transposon Tn10 (Gatz, et al., (1991) *Mol. Gen. Genet.* 227:229-237). Stress inducible promoters include salt/water stress-inducible promoters such as P5CS (Zang, et al., (1997) *Plant Sciences* 129:81-89); cold-inducible promoters, such as, cor15a (Hajela, et al., (1990) *Plant Physiol.* 93:1246-1252), cor15b (Wlihelm, et al., (1993) *Plant Mol Biol* 23:1073-1077), wsc120 (Ouellet, et al., (1998) *FEBS Lett.* 423-324-328), ci7 (Kirch, et al., (1997) *Plant Mol Biol.* 33:897-909), ci21A (Schneider, et al., (1997) *Plant Physiol.* 113:335-45); drought-inducible promoters, such as, Trg-31 (Chaudhary, et al., (1996) *Plant Mol. Biol.* 30:1247-57), rd29 (Kasuga, et al., (1999) *Nature Biotechnology* 18:287-291); osmotic inducible promoters, such as Rab17 (Vilardell, et al., (1991) *Plant Mol. Biol.* 17:985-93) and osmotin (Raghothama, et al., (1993) *Plant Mol Biol* 23:1117-28); and heat inducible promoters, such as heat shock proteins (Barros, et al., (1992) *Plant Mol.* 19:665-75; Marrs, et al., (1993) *Dev. Genet.* 14:27-41), smHSP (Waters, et al., (1996) *J. Experimental Botany* 47:325-338), and the heat-shock inducible element from the parsley ubiquitin promoter (WO 03/102198). Other stress-inducible promoters include rip2 (U.S. Pat. No. 5,332,808 and US Publication Number 2003/0217393) and rd29a (Yamaguchi-Shinozaki, et al., (1993) *Mol. Gen. Genetics* 236:331-340). Certain promoters are inducible by wounding, including the *Agrobacterium* pmas promoter (Guevara-Garcia, et al., (1993) *Plant J.* 4(3):495-505) and the *Agrobacterium* ORF13 promoter (Hansen, et al., (1997) *Mol. Gen. Genet.* 254(3):337-343).

Additional regulatory elements active in plant cells and useful in the methods or compositions of the invention include, for example, the spinach nitrite reductase gene regulatory element (Back, et al., (1991) *Plant Mol. Biol.* 17:9); a gamma zein promoter, an oleosin ole16 promoter, a globulin I promoter, an actin I promoter, an actin cl promoter, a sucrose synthetase promoter, an INOPS promoter, an EXM5 promoter, a globulin2 promoter, a b-32, ADPG-pyrophosphorylase promoter, an LtpI promoter, an Ltp2 promoter, an oleosin ole17 promoter, an oleosin ole18 promoter, an actin 2 promoter, a pollen-specific protein promoter, a pollen-specific pectate lyase gene promoter or PG47 gene promoter, an anther specific RTS2 gene promoter, SGB6 gene promoter, or G9 gene promoter, a tapetum specific RAB24 gene promoter, an anthranilate synthase alpha subunit promoter, an alpha zein promoter, an anthranilate synthase beta subunit promoter, a dihydrodipicolinate synthase promoter, a Thi I promoter, an alcohol dehydrogenase promoter, a cab binding protein promoter, an H3C4 promoter, a RUBISCO SS starch branching enzyme promoter, an actin3 promoter, an actin7 promoter, a regulatory protein GF14-12 promoter, a ribosomal protein L9 promoter, a cellulose biosynthetic enzyme promoter, an S-adenosyl-L-homocysteine hydrolase promoter, a superoxide dismutase promoter, a C-kinase receptor promoter, a phosphoglycerate mutase promoter, a root-specific RCc3 mRNA promoter, a glucose-6 phosphate isomerase promoter, a pyrophosphate-fructose 6-phosphate-1-phosphotransferase promoter, a beta-ketoacyl-ACP synthase promoter, a 33 kDa photosystem 11 promoter, an oxygen evolving protein promoter, a 69 kDa vacuolar ATPase subunit promoter, a glyceraldehyde-3-phosphate dehydrogenase promoter, an ABA- and ripening-inducible-like protein promoter, a phenylalanine ammonia lyase promoter, an adenosine triphosphatase S-adenosyl-L-homocysteine hydrolase promoter, a chalcone synthase promoter, a zein promoter, a globulin-1 promoter, an auxin-binding protein promoter, a UDP glucose flavonoid glycosyl-transferase gene promoter, an NTI promoter, an actin promoter, and an opaque 2 promoter.

An exogenous nucleic acid molecule can be introduced into a cell as a naked DNA molecule, can be incorporated in a matrix such as a liposome or a particle such as a viral particle, or can be incorporated into a vector. Incorporation of the polynucleotide into a vector can facilitate manipulation of the polynucleotide, or introduction of the polynucleotide into a plant cell. Accordingly, the vector can be derived from a plasmid or can be a viral vector such as a T-DNA vector (Horsch, et al., (1985) *Science* 227:1229-1231). If desired, the vector can include components of a plant transposable element, for example, a Ds transposon (Bancroft and Dean, (1993) *Genetics* 134:1221-1229) or an Spm transposon (Aarts, et al., (1995) *Mol. Gen. Genet.* 247:555-564). In addition to containing the transgene of interest, the vector also can contain various nucleotide sequences that facilitate, for example, rescue of the vector from a transformed plant cell; passage of the vector in a host cell, which can be a plant, animal, bacterial, or insect host cell; or expression of an encoding nucleotide sequence in the vector, including all or a portion of a rescued coding region. As such, a vector can contain any of a number of additional transcription and translation elements, including constitutive and inducible promoters, enhancers, and the like (see, for example, Bitter, et al., (1987) *Meth. Enzymol.* 153:516-544). For example, a vector can contain elements useful for passage, growth or expression in a bacterial system, including a bacterial origin of replication; a promoter, which can be an inducible promoter; and the like. A vector also can contain one or more restriction endonuclease recognition and cleavage sites, including, for example, a polylinker sequence, to facilitate insertion or removal of a transgene.

In addition to, or alternatively to, a nucleotide sequence relevant to a fertility gene (e.g., an hpRNA comprising an inverted repeat of a fertility gene promoter, or a coding sequence of a fertility gene, alone or operably linked to a heterologous promoter), an exogenous nucleic acid molecule, or a vector containing such a transgene, can contain one or more other expressible nucleotide sequences encoding an RNA or a polypeptide of interest. For example, the additional nucleotide sequence can encode an antisense nucleic acid molecule; an enzyme such as β-galactosidase, β-glucuronidase, luciferase, alkaline phosphatase, glutathione α-transferase, chloramphenicol acetyltransferase, guanine xanthine phosphoribosyltransferase, and neomycin phosphotransferase; a viral polypeptide or a peptide portion thereof; or a plant growth factor or hormone.

In certain embodiments, the expression vector contains a gene encoding a selection marker which is functionally linked to a promoter that controls transcription initiation. For a general description of plant expression vectors and reporter genes, see, Gruber, et al., "Vectors for Plant Transformation" in *Methods of Plant Molecular Biology and Biotechnology* 89-119 (CRC Press, 1993). In using the term, it is meant to include all types of selection markers, whether they be scorable or selective. Expression of such a nucleotide sequence can provide a means for selecting for a cell containing the construct, for example, by conferring a desirable phenotype to a plant cell containing the nucleotide sequence. For example, the additional nucleotide sequence can be, or encode, a selectable marker, which, when present or expressed in a plant cell, provides a means to identify the plant cell containing the marker.

A selectable marker provides a means for screening a population of organisms or cells of an organism (e.g., plants or plant cells) to identify those having the marker and, therefore, the transgene of interest. A selectable marker generally confers a selective advantage to the cell, or to an organism (e.g., a plant) containing the cell, for example, the ability to grow in the presence of a negative selective agent such as an antibiotic or, for a plant, an herbicide. A selective advantage also can be due, for example, to an enhanced or novel capacity to utilize an added compound as a nutrient, growth factor or energy source. A selective advantage can be conferred by a single polynucleotide, or its expression product, or by a combination of polynucleotides whose expression in a plant cell gives the cell a positive selective advantage, a negative selective advantage, or both. It should be recognized that expression of the transgene of interest (e.g., encoding a hpRNA) also provides a means to select cells containing the encoding nucleotide sequence. However, the use of an additional selectable marker, which, for example, allows a plant cell to survive under otherwise toxic conditions, provides a means to enrich for transformed plant cells containing the desired transgene. Examples of suitable scorable or selection genes known in the art can be found in, for example, Jefferson, et al., (1991) in *Plant Molecular Biology Manual*, ed. Gelvin, et al., (Kluwer Academic Publishers), pp. 1-33; DeWet, et al., (1987) *Mol. Cell. Biol.* 7:725-737; Goff, et al., (1990) *EMBO J.* 9:2517-2522; Kain, et al., (1995) *BioTechniques* 19:650-655; and Chiu, et al., (1996) *Curr. Biol.* 6:325-330.

Examples of selectable markers include those that confer resistance to antimetabolites such as herbicides or antibiotics, for example, dihydrofolate reductase, which confers resistance to methotrexate (Reiss, (1994) *Plant Physiol.* (Life Sci. Adv.) 13:143-149; see also, Herrera-Estrella, et al., (1983) *Nature* 303:209-213; Meijer, et al., (1991) *Plant Mol. Biol.* 16:807-820); neomycin phosphotransferase, which confers resistance to the aminoglycosides neomycin, kanamycin and paromycin (Herrera-Estrella, (1983) *EMBO J.* 2:987-995) and hygro, which confers resistance to hygromycin (Marsh, (1984) *Gene* 32:481-485; see also, Waldron, et al., (1985) *Plant Mol. Biol.* 5:103-108; Zhijian, et al., (1995) *Plant Science* 108:219-227); trpB, which allows cells to utilize indole in place of tryptophan; hisD, which allows cells to utilize histinol in place of histidine (Hartman, (1988) *Proc. Natl. Acad. Sci. USA* 85:8047); mannose-6-phosphate isomerase which allows cells to utilize mannose (WO 94/20627); ornithine decarboxylase, which confers resistance to the ornithine decarboxylase inhibitor, 2-(difluoromethyl)-DL-ornithine (DFMO; McConlogue, 1987, In: Current Communications in Molecular Biology, Cold Spring Harbor Laboratory ed.); and deaminase from *Aspergillus terreus*, which confers resistance to Blasticidin S (Tamura, (1995) *Biosci. Biotechnol. Biochem.* 59:2336-2338). Additional selectable markers include, for example, a mutant EPSPV-synthase, which confers glyphosate resistance (Hinchee, et al., (1998) *BioTechnology* 91:915-922), a mutant acetolactate synthase, which confers imidazolinone or sulfonylurea resistance (Lee, et al., (1988) *EMBO J.* 7:1241-1248), a mutant psbA, which confers resistance to atrazine (Smeda, et al., (1993) *Plant Physiol.* 103: 911-917), or a mutant protoporphyrinogen oxidase (see, U.S. Pat. No. 5,767,373), or other markers conferring resistance to an herbicide such as glufosinate. Examples of suitable selectable marker genes include, but are not limited to, genes encoding resistance to chloramphenicol (Herrera-Estrella, et al., (1983) *EMBO J.* 2:987-992); streptomycin (Jones, et al., (1987) *Mol. Gen. Genet.* 210:86-91); spectinomycin (Bretagne-Sagnard, et al., (1996) *Transgenic Res.* 5:131-137); bleomycin (Hille, et al., (1990) *Plant Mol. Biol.* 7:171-176); sulfonamide (Guerineau, et al., (1990) *Plant Mol. Biol.* 15:127-136); bromoxynil (Stalker, et al., (1988) *Science* 242:419-423); glyphosate (Shaw, et al., (1986) *Science* 233:478-481); phosphinothricin (DeBlock, et al., (1987) *EMBO J.* 6:2513-2518), and the like. One option for use of a selective gene is a glufosinate-resistance encoding DNA and in one embodiment can be the phosphinothricin acetyl transferase ("PAT"), maize optimized PAT gene or bar gene under the control of the CaMV 35S or ubiquitin promoters. The genes confer resistance to bialaphos. See, Gordon-Kamm, et al., (1990) *Plant Cell* 2:603; Uchimiya, et al., (1993) *BioTechnology* 11:835; White, et al., (1990) *Nucl Acids Res.* 18:1062; Spencer, et al., (1990) *Theor. Appl. Genet.* 79:625-631; and Anzai, et al., (1989) *Mol. Gen. Gen.* 219:492). A version of the PAT gene is the maize optimized PAT gene, described at U.S. Pat. No. 6,096,947.

In addition, markers that facilitate identification of a plant cell containing the polynucleotide encoding the marker include, for example, luciferase (Giacomin, (1996) *Plant Sci.* 116:59-72; Scikantha, (1996) *J. Bacteriol.* 178:121), green fluorescent protein (Gerdes, (1996) *FEBS Lett.* 389:44-47; Chalfie, et al., (1994) *Science* 263:802), and other fluorescent protein variants, or β-glucuronidase (Jefferson, (1987) *Plant Mol. Biol. Rep.* 5:387; Jefferson, et al., (1987) *EMBO J.* 6:3901-3907; Jefferson, (1989) *Nature* 342(6251):837-838); the maize genes regulating pigment production (Ludwig, et al., (1990) *Science* 247:449; Grotewold, et al., (1991) *PNAS* 88:4587-4591; Cocciolone, et al., (2001) *Plant J* 27(5):467-478; Grotewold, et al., (1998) Plant Cell 10:721-740); β-galactosidase (Teeri, et al., (1989) *EMBO J.* 8:343-350);

luciferase (Ow, et al., (1986) *Science* 234:856-859); chloramphenicol acetyltransferase (CAT) (Lindsey and Jones, (1987) *Plant Mol. Biol.* 10:43-52); and numerous others as disclosed herein or otherwise known in the art. Such markers also can be used as reporter molecules. Many variations on promoters, selectable markers and other components of the construct are available to one skilled in the art.

The term "plant" is used broadly herein to include any plant at any stage of development, or to part of a plant, including a plant cutting, a plant cell, a plant cell culture, a plant organ, a plant seed, and a plantlet. A plant cell is the structural and physiological unit of the plant, comprising a protoplast and a cell wall. A plant cell can be in the form of an isolated single cell or aggregate of cells such as a friable callus, or a cultured cell, or can be part of a higher organized unit, for example, a plant tissue, plant organ, or plant. Thus, a plant cell can be a protoplast, a gamete producing cell, or a cell or collection of cells that can regenerate into a whole plant. As such, a seed, which comprises multiple plant cells and is capable of regenerating into a whole plant, is considered a plant cell for purposes of this disclosure. A plant tissue or plant organ can be a seed, protoplast, callus, or any other groups of plant cells that is organized into a structural or functional unit. Particularly useful parts of a plant include harvestable parts and parts useful for propagation of progeny plants. A harvestable part of a plant can be any useful part of a plant, for example, flowers, pollen, seedlings, tubers, leaves, stems, fruit, seeds, roots, and the like. A part of a plant useful for propagation includes, for example, seeds, fruits, cuttings, seedlings, tubers, rootstocks, and the like.

A transgenic plant can be regenerated from a genetically modified plant cell, i.e., a whole plant can be regenerated from a plant cell; a group of plant cells; a protoplast; a seed; or a piece of a plant such as a leaf, a cotyledon or a cutting. Regeneration from protoplasts varies among species of plants. For example, a suspension of protoplasts can be made and, in certain species, embryo formation can be induced from the protoplast suspension, to the stage of ripening and germination. The culture media generally contain various components necessary for growth and regeneration, including, for example, hormones such as auxins and cytokinins; and amino acids such as glutamic acid and proline, depending on the particular plant species. Efficient regeneration will depend, in part, on the medium, the genotype, and the history of the culture, and is reproducible if these variables are controlled.

Regeneration can occur from plant callus, explants, organs or plant parts. Transformation can be performed in the context of organ or plant part regeneration. (see, *Meth. Enzymol. Vol.* 118; Klee, et al., (1987) *Ann. Rev. Plant Physiol.* 38:467). Utilizing the leaf disk-transformation-regeneration method, for example, disks are cultured on selective media, followed by shoot formation in about two to four weeks (see, Horsch, et al., supra, 1985). Shoots that develop are excised from calli and transplanted to appropriate root-inducing selective medium. Rooted plantlets are transplanted to soil as soon as possible after roots appear. The plantlets can be repotted as required, until reaching maturity.

In seed-propagated crops, mature transgenic plants can be self-pollinated to produce a homozygous inbred plant. The resulting inbred plant produces seeds that contain the introduced transgene, and can be grown to produce plants that express the polypeptide. Methods for breeding plants and selecting for crossbred plants having desirable characteristics or other characteristics of interest include those disclosed herein and others well known to plant breeders.

In various aspects of the present invention, one or more transgenes is introduced into cells. When used in reference to a transgene, the term "introducing" means transferring the exogenous nucleic acid molecule into a cell. A nucleic acid molecule can be introduced into a plant cell by a variety of methods. For example, the transgene can be contained in a vector, can be introduced into a plant cell using a direct gene transfer method such as electroporation or microprojectile mediated transformation, or using *Agrobacterium* mediated transformation. As used herein, the term "transformed" refers to a plant cell containing an exogenously introduced nucleic acid molecule.

One or more exogenous nucleic acid molecules can be introduced into plant cells using any of numerous well-known and routine methods for plant transformation, including biological and physical plant transformation protocols (see, e.g., Miki, et al., "Procedures for Introducing Foreign DNA into Plants"; In *Methods in Plant Molecular Biology and Biotechnology*, Glick and Thompson, Eds. (CRC Press, Inc., Boca Raton, 1993) pages 67-88). In addition, expression vectors and in vitro culture methods for plant cell or tissue transformation and regeneration of plants are routine and well-known (see, e.g., Gruber, et al., "Vectors for Plant Transformation"; Id. at pages 89-119).

Suitable methods of transforming plant cells include microinjection, Crossway, et al., (1986) *Biotechniques* 4:320-334; electroporation, Riggs, et al., (1986) *Proc. Natl. Acad. Sci. USA* 83:5602-5606; *Agrobacterium*-mediated transformation, see, for example, Townsend, et al., U.S. Pat. No. 5,563,055; direct gene transfer, Paszkowski, et al., (1984) *EMBO J.* 3:2717-2722; and ballistic particle acceleration, see, for example, Sanford, et al., U.S. Pat. No. 4,945,050; Tomes, et al., (1995) in *Plant Cell, Tissue, and Organ Culture: Fundamental Methods*, ed. Gamborg and Phillips (Springer-Verlag, Berlin); and McCabe, et al., (1988) *Bio-technology* 6:923-926. Also see, Weissinger, et al., (1988) *Annual Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); Klein, et al., (1988) *Plant Physiol.* 91:440-444 (maize); Fromm, et al., (1990) *Biotechnology* 8:833-839; Hooydaas-Van Slogteren, et al., (1984) *Nature* (London) 311:763-764; Bytebier, et al., (1987) *Proc. Natl. Acad. Sci. USA* 84:5345-5349 (Liliaceae); De Wet, et al., (1985) in *The Experimental Manipulation of Ovule Tissues*, ed. G. P. Chapman, et al., (Longman, New York), pp. 197-209 (pollen); Kaeppler, et al., (1990) *Plant Cell Reports* 9:415-418; and Kaeppler, et al., (1992) *Theor. Appl. Genet.* 84:560-566 (whisker-mediated transformation); D. Halluin, et al., (1992) *Plant Cell* 4:1495-1505 (electroporation); Li, et al., (1993) *Plant Cell Reports* 12:250-255 and Christou, et al., (1995) *Annals of Botany* 75:407-413 (rice); Osjoda, et al., (1996) *Nature Biotechnology* 14:745-750 (maize via *Agrobacterium tumefaciens*); all of which are herein incorporated by reference.

*Agrobacterium*-mediated transformation provides a useful method for introducing a transgene into plants (Horsch, et al., (1985) *Science* 227:1229 1985). *A. tumefaciens* and *A. rhizogenes* are plant pathogenic soil bacteria that genetically transform plant cells. The Ti and Ri plasmids of *A. tumefaciens* and *A. rhizogenes*, respectively, carry genes responsible for genetic transformation of the plant (see, e.g., Kado, (1991) *Crit. Rev. Plant Sci.* 10:1; see, also, Moloney, et al., (1989) *Plant Cell Reports* 8:238; U.S. Pat. No. 5,591,616; WO 99/47552; Weissbach and Weissbach, "Methods for Plant Molecular Biology" (Academic Press, NY 1988), section VIII, pages 421-463; Grierson and Corey, "Plant Molecular Biology" 2d Ed. (Blackie, London 1988), Chapters 7-9; see, also, Horsch, et al., supra, 1985).

With respect to *A. tumefaciens*, the wild type form contains a Ti plasmid, which directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An *Agrobacterium* based vector is a modified form of a Ti plasmid, in which the tumor-inducing functions are replaced by a nucleotide sequence of interest that is to be introduced into the plant host. Methods of using *Agrobacterium* mediated transformation include cocultivation of *Agrobacterium* with cultured isolated protoplasts; transformation of plant cells or tissues with *Agrobacterium*; and transformation of seeds, apices or meristems with *Agrobacterium*. In addition, in planta transformation by *Agrobacterium* can be performed using vacuum infiltration of a suspension of *Agrobacterium* cells (Bechtold, et al., (1993) *C.R. Acad. Sci. Paris* 316:1194).

*Agrobacterium*-mediated transformation can employ cointegrate vectors or binary vector systems, in which the components of the Ti plasmid are divided between a helper vector, which resides permanently in the *Agrobacterium* host and carries the virulence genes, and a shuttle vector, which contains the gene of interest bounded by T-DNA sequences. Binary vectors are well known in the art (see, for example, De Framond, (1983) *BioTechnology* 1:262; Hoekema, et al., (1983) *Nature* 303:179) and are commercially available (Clontech; Palo Alto Calif.). For transformation, *Agrobacterium* can be cocultured, for example, with plant cells or wounded tissue such as leaf tissue, root explants, hypocotyls, cotyledons, stem pieces or tubers (see, for example, Glick and Thompson, "Methods in Plant Molecular Biology and Biotechnology" (Boca Raton Fla., CRC Press 1993)). Wounded cells within the plant tissue that have been infected by *Agrobacterium* can develop organs de novo when cultured under the appropriate conditions; the resulting transgenic shoots eventually give rise to transgenic plants which contain the introduced polynucleotide.

*Agrobacterium*-mediated transformation has been used to produce a variety of transgenic plants, including, for example, transgenic cruciferous plants such as *Arabidopsis*, mustard, rapeseed and flax; transgenic leguminous plants such as alfalfa, pea, soybean, trefoil and white clover; and transgenic solanaceous plants such as eggplant, petunia, potato, tobacco and tomato (see, for example, Wang, et al., "Transformation of Plants and Soil Microorganisms" (Cambridge, University Press 1995)). In addition, *Agrobacterium* mediated transformation can be used to introduce an exogenous nucleic acid molecule into apple, aspen, belladonna, black currant, carrot, celery, cotton, cucumber, grape, horseradish, lettuce, morning glory, muskmelon, neem, poplar, strawberry, sugar beet, sunflower, walnut, asparagus, rice, wheat, sorghum, barley, maize, and other plants (see, for example, Glick and Thompson, supra, 1993; Hiei, et al., (1994) *Plant J.* 6:271-282; Shimamoto, (1995) *Science* 270: 1772-1773).

Suitable strains of *A. tumefaciens* and vectors as well as transformation of Agrobacteria and appropriate growth and selection media are well known in the art (GV3101, pMK90RK), Koncz, (1986) *Mol. Gen. Genet.* 204:383-396; (C58C1, pGV3850kan), Deblaere, (1985) *Nucl. Acid Res.* 13:4777; Bevan, (1984) *Nucleic Acid Res.* 12:8711; Koncz, (1986) *Proc. Natl. Acad. Sci. USA* 86:8467-8471; Koncz, (1992) *Plant Mol. Biol.* 20:963-976; Koncz, Specialized vectors for gene tagging and expression studies. In: Plant Molecular Biology Manual Vol. 2, Gelvin and Schilperoort (Eds.), Dordrecht, The Netherlands: Kluwer Academic Publ. (1994), 1-22; European Patent A-1 20 516; Hoekema: The Binary Plant Vector System, Offsetdrukkerij Kanters B.V., Alblasserdam (1985), Chapter V; Fraley, *Crit. Rev. Plant. Sci.*, 4:1-46; An, (1985) *EMBO J.* 4:277-287).

As noted herein, the present invention provides vectors capable of expressing genes of interest under the control of the regulatory elements. In general, the vectors should be functional in plant cells. At times, it may be preferable to have vectors that are functional in *E. coli* (e.g., production of protein for raising antibodies, DNA sequence analysis, construction of inserts, obtaining quantities of nucleic acids). Vectors and procedures for cloning and expression in *E. coli* are discussed in Sambrook, et al., (supra).

The transformation vector, comprising the promoter of the present invention operably linked to an isolated nucleotide sequence in an expression cassette, can also contain at least one additional nucleotide sequence for a gene to be co-transformed into the organism. Alternatively, the additional sequence(s) can be provided on another transformation vector.

Where the exogenous nucleic acid molecule is contained in a vector, the vector can contain functional elements, for example "left border" and "right border" sequences of the T-DNA of *Agrobacterium*, which allow for stable integration into a plant genome. Furthermore, methods and vectors that permit the generation of marker-free transgenic plants, for example, where a selectable marker gene is lost at a certain stage of plant development or plant breeding, are known, and include, for example, methods of co-transformation (Lyznik, (1989) *Plant Mol. Biol.* 13:151-161; Peng, (1995) *Plant Mol. Biol.* 27:91-104), or methods that utilize enzymes capable of promoting homologous recombination in plants (see, e.g., WO97/08331; Bayley, (1992) *Plant Mol. Biol.* 18:353-361; Lloyd, (1994) *Mol. Gen. Genet.* 242:653-657; Maeser, (1991) *Mol. Gen. Genet.* 230:170-176; Onouchi, (1991) *Nucl. Acids Res.* 19:6373-6378; see, also, Sambrook, et al., supra, 1989).

Direct gene transfer methods also can be used to introduce the desired transgene (or transgenes) into cells, including plant cells that are refractory to *Agrobacterium*-mediated transformation (see, e.g., Hiei, et al., (1994) *Plant J.* 6:271-282; U.S. Pat. No. 5,591,616). Such methods include direct gene transfer (see, European Patent Number A 164 575), injection, electroporation, biolistic methods such as particle bombardment, pollen-mediated transformation, plant RNA virus-mediated transformation, liposome-mediated transformation, transformation using wounded or enzyme-degraded immature embryos, or wounded or enzyme-degraded embryogenic callus, and the like. Direct gene transfer methods include microprojectile-mediated (biolistic) transformation methods, wherein the transgene is carried on the surface of microprojectiles measuring 1 to 4 mm. A vector, particularly an expression vector containing the transgene(s) of interest, is introduced into plant tissues with a biolistic device that accelerates the microprojectiles to speeds of 300 to 600 m/s, sufficient to penetrate plant cell walls and membranes (see, e.g., Sanford, et al., (1987) *Part. Sci. Technol.* 5:27; Sanford, (1988) *Trends Biotech.* 6:299, Klein, et al., (1988) *BioTechnology* 6:559-563; Klein, et al., (1992) *BioTechnology* 10:268). In maize, for example, several target tissues can be bombarded with DNA-coated microprojectiles in order to produce transgenic plants, including, for example, callus (Type I or Type II), immature embryos, and meristem tissue.

Other methods for physical delivery of a transgene into plants utilize sonication of the target cells (Zhang, et al., (1991) *BioTechnology* 9:996); liposomes or spheroplast fusion (Deshayes, et al., (1985) *EMBO J.* 4:2731; Christou, et al., (1987) *Proc Natl. Acad. Sci.*, USA 84:3962); $CaCl_2$ precipitation or incubation with polyvinyl alcohol or poly-L-ornithine (Hain, et al., (1985) *Mol. Gen. Genet.* 199:61; Draper, et al., (1982) *Plant Cell Physiol.* 23:451); and electroporation of protoplasts and whole cells and tissues (Donn, et al., (1990) In "Abstracts of VIIIth International Congress on Plant Cell and Tissue Culture" IAPTC, A2-38, pg. 53; D'Halluin, et al., (1992) *Plant Cell* 4:1495-1505; Spencer, et al., (1994) *Plant Mol. Biol.* 24:51-61).

A direct gene transfer method such as electroporation can be particularly useful for introducing exogenous nucleic acid molecules into a cell such as a plant cell. For example, plant protoplasts can be electroporated in the presence of a recombinant nucleic acid molecule, which can be in a vector (Fromm, et al., (1985) *Proc. Natl. Acad. Sci., USA* 82:5824). Electrical impulses of high field strength reversibly permeabilize membranes allowing the introduction of the nucleic acid. Electroporated plant protoplasts reform the cell wall, divide and form a plant callus. Microinjection can be performed as described in Potrykus and Spangenberg (eds.), Gene Transfer To Plants. Springer Verlag, Berlin, N.Y. (1995). A transformed plant cell containing the introduced recombinant nucleic acid molecule can be identified due to the presence of a selectable marker included in the construct.

As mentioned above, microprojectile mediated transformation also provides a useful method for introducing exogenous nucleic acid molecules into a plant cell (Klein et al., *Nature* 327:70-73, 1987). This method utilizes microprojectiles such as gold or tungsten, which are coated with the desired nucleic acid molecule by precipitation with calcium chloride, spermidine or polyethylene glycol. The microprojectile particles are accelerated at high speed into a plant tissue using a device such as the BIOLISTIC PD-1000 particle gun (BioRad; Hercules Calif.). Microprojectile mediated delivery ("particle bombardment") is especially useful to transform plant cells that are difficult to transform or regenerate using other methods. Methods for the transformation using biolistic methods are well known (Wan, (1984) *Plant Physiol.* 104:37-48; Vasil, (1993) *BioTechnology* 11:1553-1558; Christou, (1996) *Trends in Plant Science* 1:423-431). Microprojectile mediated transformation has been used, for example, to generate a variety of transgenic plant species, including cotton, tobacco, corn, wheat, oat, barley, sorghum, rice, hybrid poplar and papaya (see, Glick and Thompson, supra, 1993; Duan, et al., (1996) *Nature Biotech.* 14:494-498; Shimamoto, (1994) *Curr. Opin. Biotech.* 5:158-162).

A rapid transformation regeneration system for the production of transgenic plants such as a system that produces transgenic wheat in two to three months (see, European Patent Number EP 0709462A2) also can be useful for producing a transgenic plant according to a method of the invention, thus allowing more rapid identification of gene functions. The transformation of most dicotyledonous plants is possible with the methods described above. Transformation of monocotyledonous plants also can be transformed using, for example, biolistic methods as described above, protoplast transformation, electroporation of partially permeabilized cells, introduction of DNA using glass fibers, *Agrobacterium* mediated transformation, and the like.

Plastid transformation also can be used to introduce a nucleic acid molecule into a plant cell (U.S. Pat. Nos. 5,451,513, 5,545,817 and 5,545,818; WO 95/16783; McBride, et al., (1994) *Proc. Natl. Acad. Sci.*, USA 91:7301-7305). Chloroplast transformation involves introducing regions of cloned plastid DNA flanking a desired nucleotide sequence, for example, a selectable marker together with polynucleotide of interest, into a suitable target tissue, using, for example, a biolistic or protoplast transformation method (e.g., calcium chloride or PEG mediated transformation). One to 1.5 kb flanking regions ("targeting sequences") facilitate homologous recombination with the plastid genome, and allow the replacement or modification of specific regions of the plastome. Using this method, point mutations in the chloroplast 16S rRNA and rps12 genes, which confer resistance to spectinomycin and streptomycin and can be utilized as selectable markers for transformation (Svab, et al., (1990) *Proc. Natl. Acad. Sci.*, USA 87:8526-8530; Staub and Maliga, (1992) *Plant Cell* 4:39-45), resulted in stable homoplasmic transformants, at a frequency of approximately one per 100 bombardments of target leaves. The presence of cloning sites between these markers allowed creation of a plastid targeting vector for introduction of foreign genes (Staub and Maliga, (1993) *EMBO J.* 12:601-606). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab and Maliga, (1993) *Proc. Natl. Acad. Sci.*, USA 90:913-917). Approximately 15 to 20 cell division cycles following transformation are generally required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein.

The cells that have been transformed can be grown into plants in accordance with conventional ways. See, for example, McCormick, et al., (1986) *Plant Cell Reports* 5:81-84. These plants can then be grown and pollinated with the same transformed strain or different strains, and resulting plants having expression of the desired phenotypic characteristic can then be identified. Two or more generations can be grown to ensure that expression of the desired phenotypic characteristic is stably maintained and inherited.

Plants suitable for purposes of the present invention can be monocots or dicots and include, but are not limited to, maize, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugar beet, sunflower, rapeseed, clover, tobacco, carrot, cotton, alfalfa, rice, potato, eggplant, cucumber, *Arabidopsis thaliana*, and woody plants such as coniferous and deciduous trees. Thus, a transgenic plant or genetically modified plant cell of the invention can be an angiosperm or gymnosperm.

Angiosperms are divided into two broad classes based on the number of cotyledons, which are seed leaves that generally store or absorb food; a monocotyledonous angiosperm has a single cotyledon, and a dicotyledonous angiosperm has two cotyledons. Angiosperms produce a variety of useful products including materials such as lumber, rubber, and paper; fibers such as cotton and linen; herbs and medicines such as quinine and vinblastine; ornamental flowers such as roses and, where included within the scope of the present invention, orchids; and foodstuffs such as grains, oils, fruits and vegetables. Angiosperms encompass a variety of flowering plants, including, for example, cereal plants, leguminous plants, oilseed plants, hardwood trees, fruit-bearing plants and ornamental flowers, which general classes are not necessarily exclusive. Cereal plants, which produce an edible grain, include, for example, corn, rice, wheat, barley, oat, rye, orchardgrass, guinea grass, and sorghum. Leguminous plants include members of the pea family (Fabaceae) and produce a characteristic fruit known as a legume. Examples of leguminous plants include, for example, soybean, pea, chickpea, moth bean, broad bean, kidney bean, lima bean, lentil, cowpea, dry bean, and peanut, as well as alfalfa, birdsfoot trefoil, clover and sainfoin. Oilseed plants, which have seeds that are useful as a source of oil, include soybean, sunflower, rapeseed (canola) and cottonseed. Angiosperms also include hardwood trees, which are perennial woody plants that generally have a single stem (trunk). Examples of such trees include alder, ash, aspen, basswood (linden), beech, birch, cherry, cottonwood, elm, eucalyptus, hickory, locust, maple, oak, persimmon, poplar, sycamore, walnut, *sequoia*, and willow. Trees are useful, for example, as a source of pulp, paper, structural material and fuel.

Angiosperms produce seeds enclosed within a mature, ripened ovary. An angiosperm fruit can be suitable for human or animal consumption or for collection of seeds to propagate the species. For example, hops are a member of the mulberry family that are prized for their flavoring in malt liquor. Fruit-bearing angiosperms also include grape, orange, lemon, grapefruit, avocado, date, peach, cherry, olive, plum, coconut, apple and pear trees and blackberry, blueberry, raspberry, strawberry, pineapple, tomato, cucumber and eggplant plants. An ornamental flower is an angiosperm cultivated for its decorative flower. Examples of commercially important ornamental flowers include rose, lily, tulip and chrysanthemum, snapdragon, camellia, carnation and petunia plants, and can include orchids. It will be recognized that the present invention also can be practiced using gymnosperms, which do not produce seeds in a fruit.

Certain embodiments of this invention overcome the problem of maintenance of homozygous recessive reproductive traits when using a transgenic restoration approach, while decreasing the number of plants, plantings and steps needed for maintenance of plants with such traits.

Homozygosity is a genetic condition existing when identical alleles reside at corresponding loci on homologous chromosomes. Heterozygosity is a genetic condition existing when different alleles reside at corresponding loci on homologous chromosomes. Hemizygosity is a genetic condition existing when there is only one copy of a gene (or set of genes) with no allelic counterpart on the sister chromosome.

Maintenance of the homozygous recessive condition for male sterility is achieved by introducing into a plant a restoration transgene construct that is linked to a sequence which interferes with the formation, function, or dispersal of male gametes of the plant, to create a "maintainer" or "donor" plant. The restoring transgene, upon introduction into a plant that is homozygous recessive for the male sterility genetic trait, restores the genetic function of that trait. Due to the linked gene driven by a male-gamete-specific-promoter, all pollen containing the restoration transgene is rendered non-viable. All viable pollen produced contains a copy of the recessive allele but does not contain the restoration transgene. The transgene is kept in the hemizygous state in the maintainer plant.

The pollen from the maintainer can be used to fertilize plants that are homozygous for the recessive trait, and the progeny will therefore retain their homozygous recessive condition. The maintainer plant containing the restoring transgene construct is propagated by self-fertilization, with half of the resulting seed used to produce further plants that are homozygous recessive for the gene of interest and hemizygous for the restoring transgene construct.

The maintainer plant serves as a pollen donor to the plant having the homozygous recessive trait. The maintainer is optimally produced from a plant having the homozygous recessive trait and which also has nucleotide sequences introduced therein which would restore the trait created by the homozygous recessive alleles. Further, the restoration sequence is linked to nucleotide sequences that interfere with the function, formation, or dispersal of male gametes. The gene can operate to prevent formation of male gametes or prevent function of the male gametes by any of a variety of well-known modalities and is not limited to a particular methodology. By way of example but not limitation, this can include use of one or more genes which express a product cytotoxic to male gametes (see, for example, U.S. Pat. Nos. 5,792,853; and 5,689,049; PCT/EP89/00495); inhibit product formation of another gene important to male gamete formation, function, or dispersal (see, U.S. Pat. Nos. 5,859,341 and 6,297,426); combine with another gene product to produce a substance preventing gamete formation, function, or dispersal (see, U.S. Pat. Nos. 6,162,964; 6,013,859; 6,281,348; 6,399,856; 6,248,935; 6,750,868 and 5,792,853); are antisense to or cause co-suppression of a gene critical to male gamete formation, function, or dispersal (see, U.S. Pat. Nos. 6,184,439; 5,728,926; 6,191,343; 5,728,558 and 5,741,684), or the like.

Ordinarily, to produce more plants having the recessive condition, one might cross the recessive plant with another recessive plant, or self pollinate a recessive plant. This may not be desirable for some recessive traits and may be impossible for recessive traits affecting reproductive development. Alternatively, one could cross the homozygous plant with a second plant having the restoration gene, but this requires further crossing to segregate away the restoring gene to once again reach the recessive phenotypic state. Instead, in one embodiment the invention provides a process in which the homozygous recessive condition can be maintained, while crossing it with the maintainer plant. This method can be used with any situation in which it is desired to continue the recessive condition. This results in a relatively simple, cost-effective system for maintaining a population of homozygous recessive plants.

When the homozygous recessive condition is one that produces male sterility, the maintainer plant, of necessity, must contain a functional restoring transgene construct capable of complementing the mutation and rendering the homozygous recessive plant able to produce viable pollen. Linking this male fertility restoration gene with a second functional nucleotide sequence which interferes with the formation, function, or dispersal of the male gametes of the plant results in a maintainer plant that produces pollen containing only the recessive allele of the restored gene at its native locus due to the pollen-specific cytotoxic action of the second nucleotide sequence. This viable pollen fraction is non-transgenic with regard to the restoring transgene construct.

For example, it is desirable to produce male sterile female plants for use in the hybrid production process which are sterile as a result of being homozygous for a mutation in the MS45 gene, a gene which is essential for male fertility. Such a mutant MS45 allele is designated as ms45. A plant that is homozygous for ms45 (represented by the notation ms45/ms45) displays the homozygous recessive male sterility phenotype and produces no functional pollen. See, U.S. Pat. Nos.

5,478,369; 5,850,014; 6,265,640 and 5,824,524. In both the inbred and hybrid production processes, it is highly desired to maintain this homozygous recessive condition. When sequences encoding the MS45 gene are introduced into a plant having the homozygous condition, sporophytic restoration of male fertility results. (Cigan, et al., (2001) *Sex. Plant Repro.* 14:135-142). By the method of the invention, a plant which is ms45/ms45 homozygous recessive may have introduced into it a functional MS45 gene, and thus male fertility is restored. This gene can be linked to a second gene which operates to render pollen nonfunctional or which prevents its formation, or which produces a lethal product in pollen, and which is linked to a promoter directing its expression in the male gametes. This results in a plant which produces viable pollen containing ms45 without the restoring transgene construct.

An example is a construct that includes the MS45 gene operably linked to the 5126 promoter, a male tissue-preferred promoter (see, U.S. Pat. No. 5,837,851) and further linked to the cytotoxic DAM methylase gene under control of the PG47 promoter (see, U.S. Pat. Nos. 5,792,853 and 5,689,049). The resulting plant produces pollen, but the only viable pollen contains the ms45 gene. It can therefore be used as a pollinator to fertilize the homozygous recessive plant (ms45/ms45), and 100% of the progeny produced will continue to be male sterile as a result of maintaining homozygosity for ms45. The progeny will not contain the introduced restoring transgene construct.

Clearly, many variations on this method are available as it relates to male sterility. Any other gene critical to male fertility may be used in this system. For example and without limitation, such genes can include the SBMu200 gene (also known as SB200 or MS26) described at WO 02/26789; the BS92-7 gene (also known as BS7) described at WO 02/063021; MS2 gene described at Albertsen and Phillips, "Developmental Cytology of 13 Genetic Male Sterile Loci in Maize" *Canadian Journal of Genetics & Cytology* 23:195-208 (January 1981); or the *Arabadopsis* MS2 gene described at Aarts et al., "Transposon Tagging of a Male Sterility Gene in *Arabidopsis*", *Nature,* 363:715-717 (Jun. 24, 1993); and the *Arabidopsis* gene MS1 described at Wilson, et al., "The *Arabidopsis* MALE STERILITY1 (MS1) gene is a transcriptional regulator of male gametogenesis, with homology to the PHD-finger family of transcription factors", *Plant J.,* 1:27-39 (Oct. 28, 2001).

A desirable result of the process of the invention is that the plant having the restorer nucleotide sequence may be self-fertilized; that is, pollen from the plant transferred to the flower of the same plant to achieve the propagation of restorer plants. (Note that "self fertilization" includes both the situation where the plant producing the pollen is fertilized with that same pollen, and the situation where pollen from a plant, or from a group of genetically identical plants, pollinates a plant which is a genetically identical individual, or a group of such genetically identical plants.) The restoring transgene construct will not be present in the pollen, but it will be contained in 50% of the ovules (the female gamete). The seed resulting from the self-fertilization can be planted, and selection made for the seed having the restoring transgene construct. The selection process can occur by any one or more of many known processes, the most common being where the restoration nucleotide sequence is linked to a marker gene. The marker can be scorable or selectable, and allows identification of the seed comprising the restoration sequence, and/or of those plants produced from the seed having the restoration sequence.

In an embodiment of the invention, it is possible to provide that the promoter driving the restoration gene is inducible. Additional control is thus allowed in the process, where so desired, by providing that the plant having the restoration nucleotide sequences is constitutively male sterile. This type of male sterility is set forth the in U.S. Pat. No. 5,859,341. In order for the plant to become fertile, the inducing substance must be provided, and the plant will become fertile. Again, when combined with the process of the invention as described supra, the only pollen produced will not contain the restoration nucleotide sequences.

In yet another embodiment of the invention, the gamete controlling the transmission of the restoration nucleotide sequences can be the female gamete, instead of the male gamete. The process is the same as that described above, with the exception in those instances where one also desires to maintain the plant having the restoration nucleotide sequences by self fertilization. In that case, it will be useful to provide that the promoter driving the restoration gene is inducible, so that female fertility may be triggered by exposure to the inducing substance, and seed can be formed. Control of female fertility in such a manner is described at U.S. Pat. No. 6,297,426. Examples of genes impacting female fertility include the teosinte branched1 (Tb1) gene, which increases apical dominance, resulting in multiple tassels and repression of female tissue. Hubbard, et al., (2002) Genetics 162:1927-1935; Doebley, et al., (1997) *Nature* 386:485-488 (1997). Another example is the so-called "barren3" or "ba3". This mutant was isolated from a mutant maize plant infected with wheat-streak mosaic virus and is described at Pan and Peterson, (1992) *J. Genet. And Breed.* 46:291-294. The plants develop normal tassels but do not have any ear shoots along the stalks. Barren-stalk fastigiate is described at Coe and Beckett, (1987) *Maize Genet. Coop. Newslett.* 61:46-47. Other examples include the barren stalk1 gene (Gallavotti, et al., (2004) *Nature* 432:630-635); lethal ovule mutant (Vollbrecht, (1994) *Maize Genetics Cooperation Newsletter* 68:2-3); and defective pistil mutant (Miku and Mustyatsa, (1978) *Genetika* 14(2):365-368).

Any plant-compatible promoter elements can be employed to control expression of the regions of the restoring transgene construct that encode specific proteins and functions. Those can be plant gene promoters, such as, for example, the ubiquitin promoter, the promoter for the small subunit of ribulose-1,5-bis-phosphate carboxylase, or promoters from the tumor-inducing plasmids from *Agrobacterium tumefaciens*, such as the nopaline synthase and octopine synthase promoters, or viral promoters such as the cauliflower mosaic virus (CaMV) 19S and 35S promoters or the figwort mosaic virus 35S promoter. See, Kay, et al., (1987) *Science* 236:1299 and European Patent Application Number 0 342 926. See, international application number WO 91/19806 for a review of illustrative plant promoters suitably employed in the present invention. The range of available plant-compatible promoters includes tissue-specific and inducible promoters.

The invention contemplates the use of promoters providing tissue-preferred expression, including promoters which preferentially express to the gamete tissue, male or female, of the plant. The invention does not require that any particular gamete tissue-preferred promoter be used in the process, and any of the many such promoters known to one skilled in the art may be employed. By way of example, but not limitation, one such promoter is the 5126 promoter, which preferentially directs expression of the gene to which it is linked to male tissue of the plants, as described in U.S. Pat. Nos. 5,837,851 and 5,689,051. Other examples include the MS45 promoter described at U.S. Pat. No. 6,037,523; SF3 promoter described at U.S. Pat. No. 6,452,069; the BS92-7 or BS7 promoter described at WO 02/063021; the SBMu200 promoter described at WO 02/26789; a SGB6 regulatory element described at U.S. Pat. No. 5,470,359, and TA39 (Koltunow, et al., (1990) "Different temporal and spatial gene expression patterns occur during anther development." *Plant Cell* 2:1201-1224; Goldberg, et al., (1993) Anther development: basic principles and practical applications. *Plant Cell* 5:1217-1229; and U.S. Pat. No. 6,399,856. See also, Nadeau, et al., (1996) *Plant Cell* 8(2):213-39; and Lu, et al., (1996) *Plant Cell* 8(12):2155-68.

The P67 promoter set forth in SEQ ID NO: 1 is 1112 nucleotides in length. This promoter was isolated from a genomic clone corresponding to a maize EST sequence. The sequence showed limited homology to putative pectin methylesterase.

The pollen specificity of expression of P67 has been confirmed by RT-PCR and Northern blot analyses of RNA samples from different tissues including leaf, root, anther/mature pollen grains, tassel at vacuole stage, spikelet, cob, husk, silk and embryo. The results indicate a high level of specificity for expression in developing pollen, particularly at the mid-uninucleate stage.

Southern blot analysis has shown that the clone represents single- or low-copy genes in the corn genome. Chromosome mapping using the oat chromosome substitution line revealed that the sequence is located at Chromosome 1 of maize.

The clone was used to screen a maize BAC library. Positive BAC clones have been found and subcloned into pBluescript KS. Subclones corresponding to the cDNA sequences have been identified and sequenced. The transcriptional start site has been determined using a RNA ligase-mediated rapid amplification of 5' end approach. The promoter region was named P67.

The P95 promoter set forth in SEQ ID NO: 2 is 1092 nucleotides in length. This promoter was isolated from a genomic clone corresponding to a maize EST sequence. The sequence showed limited homology to putative L-ascorbate oxidase.

The pollen specificity of expression of P95 has been confirmed by RT-PCR and Northern blot analyses of RNA samples from different tissues including leaf, root, anther/mature pollen grains, tassel at vacuole stage, spikelet, cob, husk, silk and embryo. The results indicate a high level of specificity for expression in developing pollen, particularly at the mid-uninucleate stage.

Southern blot analysis has shown that the clone represents single- or low-copy genes in the corn genome. Chromosome mapping using the oat chromosome substitution line revealed that the sequence is located at Chromosomes 6 and 8 of maize.

The clone was used to screen a maize BAC library. Positive BAC clones have been found and subcloned into pBluescript KS. Subclones corresponding to the cDNA sequences have been identified and sequenced. The transcriptional start site has been determined using a RNA ligase-mediated rapid amplification of 5' end approach. The promoter region was named P95.

Using well-known techniques, additional promoter sequences may be isolated based on their sequence homology to SEQ ID NO: 1 or SEQ ID NO: 2. In these techniques, all or part of a known promoter sequence is used as a probe which selectively hybridizes to other sequences present in a population of cloned genomic DNA fragments (i.e. genomic libraries) from a chosen organism. Methods that are readily available in the art for the hybridization of nucleic acid sequences may be used to obtain sequences which correspond to these promoter sequences in species including, but not limited to, maize (corn; *Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats, barley, vegetables, ornamentals, and conifers. Preferably, plants include maize, soybean, sunflower, safflower, canola, wheat, barley, rye, alfalfa, and sorghum.

The entire promoter sequence or portions thereof can be used as a probe capable of specifically hybridizing to corresponding promoter sequences. To achieve specific hybridization under a variety of conditions, such probes include sequences that are unique and are preferably at least about 10 nucleotides in length, and most preferably at least about 20 nucleotides in length. Such probes can be used to amplify corresponding promoter sequences from a chosen organism by the well-known process of polymerase chain reaction (PCR). This technique can be used to isolate additional promoter sequences from a desired organism or as a diagnostic assay to determine the presence of the promoter sequence in an organism. Examples include hybridization screening of plated DNA libraries (either plaques or colonies; see e.g., Innis, et al., (1990) *PCR Protocols, A Guide to Methods and Applications*, eds., Academic Press).

In general, sequences that correspond to a promoter sequence of the present invention and hybridize to a promoter sequence disclosed herein will be at least 50% homologous, 55% homologous, 60% homologous, 65% homologous, 70% homologous, 75% homologous, 80% homologous, 85% homologous, 90% homologous, 95% homologous and even 98% homologous or more with the disclosed sequence.

Fragments of a particular promoter sequence disclosed herein may operate to promote the pollen-preferred expression of an operably-linked isolated nucleotide sequence. These fragments will comprise at least about 20 contiguous nucleotides, preferably at least about 50 contiguous nucleotides, more preferably at least about 75 contiguous nucleotides, even more preferably at least about 100 contiguous nucleotides of the particular promoter nucleotide sequences disclosed herein. The nucleotides of such fragments will usually comprise the TATA recognition sequence of the particular promoter sequence. Such fragments can be obtained by use of restriction enzymes to cleave the naturally-occurring promoter sequences disclosed herein; by synthesizing a nucleotide sequence from the naturally-occurring DNA sequence; or through the use of PCR technology. See particularly, Mullis, et al., (1987) *Methods Enzymol.* 155:335-350, and Erlich, ed. (1989) *PCR Technology* (Stockton Press, New York). Again, variants of these fragments, such as those resulting from site-directed mutagenesis, are encompassed by the compositions of the present invention.

Thus, nucleotide sequences comprising at least about 20 contiguous nucleotides of the sequence set forth in SEQ ID NO: 1 or SEQ ID NO: 2 are encompassed. These sequences can be isolated by hybridization, PCR, and the like. Such sequences encompass fragments capable of driving pollen-preferred expression, fragments useful as probes to identify similar sequences, as well as elements responsible for temporal or tissue specificity.

Biologically active variants of the promoter sequence are also encompassed by the compositions of the present invention. A regulatory "variant" is a modified form of a promoter wherein one or more bases have been modified, removed or added. For example, a routine way to remove part of a DNA sequence is to use an exonuclease in combination with DNA amplification to produce unidirectional nested deletions of double-stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at 5' overhangs, blunt ends or nicks in the DNA template. However, exonuclease III is unable to remove nucleotides at 3', 4-base overhangs. Timed digests of a clone with this enzyme produce unidirectional nested deletions.

One example of a regulatory sequence variant is a promoter formed by causing one or more deletions in a larger promoter. Deletion of the 5' portion of a promoter up to the TATA box near the transcription start site may be accomplished without abolishing promoter activity, as described by Zhu, et al., (1995) *The Plant Cell* 7:1681-89. Such variants should retain promoter activity, particularly the ability to drive expression in specific tissues. Biologically active variants include, for example, the native regulatory sequences of the invention having one or more nucleotide substitutions, deletions or insertions. Activity can be measured by Northern blot analysis, reporter activity measurements when using transcriptional fusions, and the like. See, for example, Sambrook, et al., (1989) *Molecular Cloning: A Laboratory Manual* (2nd ed. Cold Spring Harbor Laboratory, Cold Spring Harbor, N.Y.), herein incorporated by reference.

The nucleotide sequences for the pollen-preferred promoters disclosed in the present invention, as well as variants and fragments thereof, are useful in the genetic manipulation of any plant when operably linked with an isolated nucleotide sequence whose expression is to be controlled to achieve a desired phenotypic response.

The nucleotide sequence operably linked to the regulatory elements disclosed herein can be an antisense sequence for a targeted gene. By "antisense DNA nucleotide sequence" is intended a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing with the endogenous messenger RNA (mRNA) produced by transcription of the DNA nucleotide sequence for the targeted gene. In this case, production of the native protein encoded by the targeted gene is inhibited to achieve a desired phenotypic response. Thus the regulatory sequences claimed herein can be operably linked to antisense DNA sequences to reduce or inhibit expression of a native or exogenous protein in the plant.

Many nucleotide sequences are known which inhibit pollen formation or function or dispersal, and any sequences which accomplish this inhibition will suffice. A discussion of genes which can impact proper development or function is included at U.S. Pat. No. 6,399,856 and includes dominant negative genes such as cytotoxin genes, methylase genes, and growth-inhibiting genes. Dominant negative genes include diphtheria toxin A-chain gene (Czako and An (1991) *Plant Physiol.* 95:687-692); cell cycle division mutants such as CDC in maize (Colasanti, et al., (1991) *Proc. Natl. Acad. Sci. USA* 88:3377-3381); the WT gene (Farmer, et al., (1994) *Hum. Mol. Genet.* 3:723-728); and P68 (Chen, et al., (1991) *Proc. Natl. Acad. Sci. USA* 88:315-319). A suitable gene may also encode a protein involved in inhibiting pistil development, pollen stigma interactions, pollen tube growth or fertilization, or a combination thereof. In addition, genes that either interfere with the normal accumulation of starch in pollen or affect osmotic balance within pollen may also be suitable. These may include, for example, the maize alpha-amylase gene, maize beta-amylase gene, debranching enzymes such as Sugary1 and pullulanase, glucanase, and SacB.

In an illustrative embodiment, the DAM-methylase gene, the expression product of which catalyzes methylation of adenine residues in the DNA of the plant, is used. Methylated adenines will not affect cell viability and will be found only in the tissues in which the DAM-methylase gene is expressed, because such methylated residues are not found endogenously in plant DNA. Examples of so-called "cytotoxic" genes are discussed supra and can include, but are not limited to pectate lyase gene pelE, from *Erwinia chrysanthermi* (Kenn, et al., (1986) *J. Bacteriol* 168:595); diphtheria toxin A-chain gene (Greenfield, et al., (1983) *Proc. Natl. Acad. Sci. USA* 80:6853, Palmiter, et al., (1987) *Cell* 50:435); T-urf13 gene from cms-T maize mitochondrial genomes (Braun, et al., (1990) *Plant Cell* 2:153; Dewey, et al., (1987) *Proc. Natl. Acad. Sci. USA* 84:5374); CytA toxin gene from *Bacillus thuringiensis* Israeliensis that causes cell membrane disruption (McLean, et al., (1987) *J. Bacteriol* 169:1017, U.S. Pat. No. 4,918,006); DNAses, RNAses, (U.S. Pat. No. 5,633,441); proteases, or genes expressing anti-sense RNA.

Further, the methods of the invention are useful in retaining the homozygous recessive condition of traits other than those impacting plant fertility. The gene of interest which restores the condition would be introduced into a plant linked to a nucleotide sequence which inhibits the formation, function, or dispersal of pollen and which may be further linked to a male gamete tissue-preferred promoter and a gene encoding a marker, for example a seed-specific marker. Viable pollen produced by the plant into which the construct is introduced contains only the recessive allele of the gene of interest and none of the restoring transgene sequences. Half of the female gametes of the hemizygous transgenic plant contain the transgene and can be self-pollinated, or pollinated by a plant comprising the recessive alleles. Half of the seeds produced will carry the transgene and can be identified by means of the linked marker. The hemizygous condition can be maintained by selfing the hemizygous plant; half of the offspring will contain the transgene and thus the trait of interest.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increases, the choice of genes for transformation will change accordingly.

Regulation of male fertility is necessarily measured in terms of its effect on individual cells. For example, suppression in 99.99% of pollen grains is required to achieve reliable sterility for commercial use. However, successful suppression or restoration of expression of other traits may be accomplished with lower stringency. Within a particular tissue, for example, expression in 98%, 95%, 90%, 80% or fewer cells may result in the desired phenotype.

This invention has utility for a variety of recessive genes, not limited to those where expression of the homozygous recessive trait compromises the plant's ability to maintain its full reproductive capacity. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like. Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703, 049, 5,885,801, 5,885,802 and 5,990,389. Another example is lysine and/or sulfur rich seed protein encoded by the soybean 2S albumin described in U.S. Pat. No. 5,850,016, and the chymotrypsin inhibitor from barley, described in Williamson, et al., (1987) Eur. J. Biochem. 165:99-106. Other important genes encode growth factors and transcription factors.

Agronomic traits can be improved by altering expression of genes that: affect growth and development, especially during environmental stress. These include, for example, genes encoding cytokinin biosynthesis enzymes, such as isopentenyl transferase; genes encoding cytokinin catabolic enzymes, such as cytokinin oxidase; genes encoding polypeptides involved in regulation of the cell cycle, such as CyclinD or cdc25; genes encoding cytokinin receptors or sensors, such as CRE1, CKI1, and CKI2, histidine phospho-transmitters, or cytokinin response regulators.

Insect resistance genes may encode resistance to pests that have great yield drag such as rootworm, cutworm, European Corn Borer, and the like. Such genes include, for example: Bacillus thuringiensis endotoxin genes, U.S. Pat. Nos. 5,366, 892; 5,747,450; 5,737,514; 5,723,756 and 5,593,881; Geiser, et al., (1986) Gene 48:109; lectins, Van Damme, et al., (1994) Plant Mol. Biol. 24:825; and the like.

Genes encoding disease resistance traits include: detoxification genes, such as against fumonisin (WO 9606175 filed Jun. 7, 1995); avirulence (avr) and disease resistance (R) genes, Jones, et al., (1994) Science 266:789; Martin, et al., (1993) Science 262:1432; Mindrinos, et al., (1994) Cell 78:1089; and the like.

Commercial traits can also be encoded on a gene(s) which could alter or increase for example, starch for the production of paper, textiles and ethanol, or provide expression of proteins with other commercial uses. Another important commercial use of transformed plants is the production of polymers and bioplastics such as described in U.S. Pat. No. 5,602, 321 issued Feb. 11, 1997. Genes such as B-Ketothiolase, PHBase (polyhydroxybutyrate synthase) and acetoacetyl-CoA reductase (see, Schubert, et al., (1988) J. Bacteriol 170 (12):5837-5847) facilitate expression of polyhydroxyalkanoates (PHAs).

Exogenous products include plant enzymes and products as well as those from other sources including prokaryotes and other eukaryotes. Such products include enzymes, cofactors, hormones, and the like. The level of seed proteins, particularly modified seed proteins having improved amino acid distribution to improve the nutrient value of the seed, can be increased. This is achieved by the expression of such proteins having enhanced amino acid content.

Expression cassettes of the invention, comprising a promoter and isolated nucleotide sequence of interest, may also include, at the 3' terminus of the isolated nucleotide sequence of interest, a transcriptional and translational termination region functional in plants. The termination region can be native with the promoter nucleotide sequence of the cassette, can be native with the DNA sequence of interest, or can be derived from another source.

Other convenient termination regions are available from the Ti-plasmid of A. tumefaciens, such as the octopine synthase and nopaline synthase termination regions. See also, Guerineau, et al., (1991) Mol. Gen. Genet. 262:141-144; Proudfoot (1991) Cell 64:671-674; Sanfacon, et al., (1991) Genes Dev. 5:141-149; Mogen, et al., (1990) Plant Cell 2:1261-1272; Munroe, et al., (1990) Gene 91:151-158; Ballas, et al., 1989) Nucleic Acids Res. 17:7891-7903; Joshi, et al., (1987) Nucleic Acid Res. 15:9627-9639.

The expression cassettes can additionally contain 5' leader sequences. Such leader sequences can act to enhance translation. Translation leaders are known in the art and include: picornavirus leaders, for example: EMCV leader (Encephalomyocarditis 5' noncoding region), Elroy-Stein, et al., (1989) Proc. Nat. Acad. Sci. USA 86:6126-6130; potyvirus leaders, for example, TEV leader (Tobacco Etch Virus), Allison, et al., (1986); MDMV leader (Maize Dwarf Mosaic Virus), Virology 154:9-20; human immunoglobulin heavy-chain binding protein (BiP), Macejak, et al., (1991) Nature 353:90-94; untranslated leader from the coat protein mRNA of alfalfa mosaic virus (AMV RNA 4), Jobling, et al., (1987) Nature 325:622-625); tobacco mosaic virus leader (TMV), Gallie, et al., (1989) Molecular Biology of RNA, pages 237-256; and maize chlorotic mottle virus leader (MCMV) Lommel, et al., (1991) Virology 81:382-385. See also, Della-Cioppa, et al., (1987) Plant Physiology 84:965-968. The cassette can also contain sequences that enhance translation and/or mRNA stability such as introns.

In those instances where it is desirable to have the expressed product of the isolated nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to: the transit peptide for the acyl carrier protein, the small subunit of RUBISCO, plant EPSP synthase, and the like.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction digests, annealing, and resubstitutions such as transitions and transversions, can be involved.

The following terms are used to describe the sequence relationships between two or more nucleic acids or polynucleotides: (a) "reference sequence", (b) "comparison window", (c) "percentage of sequence identity", and (d) "substantial identity".

(a) As used herein, "reference sequence" is a defined sequence used as a basis for sequence comparison. A reference sequence may be a subset or the entirety of a specified sequence; for example, a segment of a full-length promoter sequence, or the complete promoter sequence.

(b) As used herein, "comparison window" makes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length and optionally can be 30, 40, 50, 100 or more contiguous nucleotides in length. Those of skill in the art understand that to avoid a high similarity to a reference sequence due to inclusion of gaps in the polynucleotide sequence, a gap penalty is typically introduced and is subtracted from the number of matches.

(c) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity.

(d) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters.

Methods of aligning sequences for comparison are well known in the art. Gene comparisons can be determined by conducting BLAST (Basic Local Alignment Search Tool; Altschul, et al., (1993) *J. Mol. Biol.* 215:403-410; see also the BLAST page of the U.S. government's National Center for Biotechnology Information, National Library of Medicine, National Institutes of Health) searches under default parameters for identity to sequences contained in the BLAST "GENEMBL" database. A sequence can be analyzed for identity to all publicly available DNA sequences contained in the GENEMBL database using the BLASTN algorithm under the default parameters.

For purposes of defining the present invention, GAP (Global Alignment Program) is used. GAP uses the algorithm of Needleman and Wunsch (*J. Mol. Biol.* 48:443-453, 1970) to find the alignment of two complete sequences that maximizes the number of matches and minimizes the number of gaps. Default gap creation penalty values and gap extension penalty values in Version 10 of the Wisconsin Package® (Accelrys, Inc., San Diego, Calif.) for protein sequences are 8 and 2, respectively. For nucleotide sequences the default gap creation penalty is 50 while the default gap extension penalty is 3. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Package® (Accelrys, Inc., San Diego, Calif.) is BLOSUM62 (see, Henikoff and Henikoff (1989) *Proc. Natl. Acad. Sci. USA* 89:10915).

Large amounts of the nucleic acids of the present invention may be produced by replication in a suitable host cell. Natural or synthetic nucleic acid fragments coding for a desired fragment will be incorporated into recombinant nucleic acid constructs, usually DNA constructs, capable of introduction into and replication in a prokaryotic or eukaryotic cell. Usually the nucleic acid constructs will be suitable for replication in a unicellular host, such as yeast or bacteria, but may also be intended for introduction to (with and without integration within the genome) cultured mammalian or plant or other eukaryotic cell lines. The purification of nucleic acids produced by the methods of the present invention is described, for example, in Sambrook, et al., Molecular Cloning. A Laboratory Manual, 2nd Ed. (Cold Spring Harbor Laboratory, Cold Spring Harbor, N.Y. (1989) or Ausubel, et al., Current Protocols in Molecular Biology, J. Wiley and Sons, NY (1992).

Nucleic acid constructs prepared for introduction into a prokaryotic or eukaryotic host may comprise a replication system recognized by the host, including the intended nucleic acid fragment encoding the desired protein, and will preferably also include transcription and translational initiation regulatory sequences operably linked to the protein encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals may also be included where appropriate. Such vectors may be prepared by means of standard recombinant techniques well known in the art and discussed, for example, in Sambrook, et al., Molecular Cloning. A Laboratory Manual, 2nd Ed. (Cold Spring Harbor Laboratory, Cold Spring Harbor, N.Y. (1989) or Ausubel, et al., Current Protocols in Molecular Biology, J. Wiley and Sons, NY (1992).

Vectors for introduction of genes both for recombination and for extrachromosomal maintenance are known in the art, and any suitable vector may be used. Methods for introducing DNA into cells such as electroporation, calcium phosphate co-precipitation, and viral transduction are known in the art, and the choice of method is within the competence of one skilled in the art (Robbins, Ed., Gene Therapy Protocols, Human Press, NJ (1997)).

Gene transfer systems known in the art may be useful in the practice of the present invention. These include viral and non-viral transfer methods. A number of viruses have been used as gene transfer vectors, including polyoma, i.e., SV40 (Madzak, et al., (1992) *J. Gen. Virol.,* 73:1533-1536), adenovirus (Berkner, (1992) *Curr. Top. Microbiol. Immunol.* 158: 39-61; Berkner, et al., (1988) *Bio Techniques,* 6:616-629; Gorziglia, et al., (1992) *J. Virol.* 66:4407-4412; Quantin, et al., (1992) *Proc. Natl. Acad. Sci. USA* 89:2581-2584; Rosenfeld, et al., (1992) *Cell* 68:143-155; Wilkinson, et al., (1992) *Nucl. Acids Res.* 20:2233-2239; Stratford-Perricaudet, et al., (1990) *Hum. Gene Ther.* 1:241-256), vaccinia virus (Mackett, et al., (1992) *Biotechnology* 24:495499), adeno-associated virus (Muzyczka, (1992) *Curr. Top. Microbiol. Immunol.* 158:91-123; Ohi, et al., (1990) *Gene* 89:279-282), herpes viruses including HSV and EBV (Margolskee, (1992) *Curr. Top. Microbiol. Immunol.* 158:67-90; Johnson, et al., (1992) *J. Virol.* 66:2952-2965; Fink, et al., (1992) *Hum. Gene Ther.* 3:11-19; Breakfield, et al., (1987) *Mol. Neurobiol.* 1:337-371; Fresse, et al., (1990) *Biochem. Pharmacol.* 40:2189-2199), and retroviruses of avian (Brandyopadhyay, et al., (1984) *Mol. Cell Biol.* 4:749-754; Petropouplos, et al., (1992) *J. Virol.* 66:3391-3397), murine (Miller, (1992) *Curr. Top. Microbiol. Immunol.* 158:1-24; Miller, et al., (1985) *Mol. Cell Biol.* 5:431-437; Sorge, et al., (1984) *Mol. Cell Biol.* 4:1730-1737; Mann, et al., (1985) *J. Virol.* 54:401-407), and human origin (Page, et al., (1990) *J. Virol.* 64:5370-5276; Buchschalcher, et al., (1992) *J. Virol.* 66:2731-2739).

Non-viral gene transfer methods known in the art include chemical techniques such as calcium phosphate coprecipitation (Graham, et al., (1973) *Virology* 52:456-467; Pellicer, et al., (1980) *Science* 209:1414-1422), mechanical techniques, for example microinjection (Anderson, et al., (1980) *Proc. Natl. Acad. Sci. USA*, 77:5399-5403; Gordon, et al., (1980) *Proc. Natl. Acad. Sci. USA*, 77:7380-7384; Brinster, et al., (1981) *Cell* 27:223-231; Constantini, et al., (1981) *Nature* 294:92-94), membrane fusion-mediated transfer via liposomes (Felgner, et al., (1987) *Proc. Natl. Acad. Sci. USA* 84:7413-7417; Wang, et al., (1989) *Biochemistry* 28:9508-9514; Kaneda, et al., (1989) *J. Biol. Chem.* 264:12126-12129; Stewart, et al., (1992) *Hum. Gene Ther.* 3:267-275; Nabel, et al., (1990) *Science* 249:1285-1288; Lim, et al., (1992) *Circulation* 83:2007-2011), and direct DNA uptake and receptor-mediated DNA transfer (Wolff, et al., (1990) *Science* 247:1465-1468; Wu, et al., (1991) *BioTechniques* 11:474-485; Zenke, et al., (1990) *Proc. Natl. Acad. Sci. USA* 87:3655-3659; Wu, et al., (1989) *J. Biol. Chem.* 264:16985-16987; Wolff, et al., (1991) *BioTechniques* 11:474485; Wagner, et al., 1990; Wagner, et al., (1991) *Proc. Natl. Acad. Sci. USA* 88:42554259; Cotton, et al., (1990) *Proc. Natl. Acad. Sci. USA* 87:4033-4037; Curiel, et al., (1991) *Proc. Natl. Acad. Sci. USA* 88:8850-8854; Curiel, et al., (1991) *Hum. Gene Ther.* 3:147-154).

One skilled in the art readily appreciates that the methods described herein are applicable to other species not specifically exemplified, including both plants and other non-human organisms. The following examples are intended to illustrate but not limit the invention.

EXAMPLE 1

Promoter Hairpin RNA Expression Affects Plant Fertility

This example demonstrates that the fertility or fertility potential of plants can be altered by expression of hairpin RNA (hpRNA) molecules specific for the promoters of genes that encode proteins involved in male fertility pathways.

Promoter hpRNA constructs were generated by linking a ubiquitin promoter to an inverted repeat of the desired promoter, including a NOS promoter segment between the inverted repeat sequences. Expression of each construct generated a hpRNA specific for one of the following promoters: MS45, 5126, BS7, SB200, and PG47. Nucleic acid molecules and methods for preparing the constructs and transforming maize were as previously described (Cigan, et al., (2001) *Sex Plant Reprod.* 14:135-142). Progeny (T1 generation) of transformed (T0) plants were analyzed.

Of 32 transformation events comprising hpRNA specific for the MS45 gene promoter, 29 produced T1 plants that were male sterile.

Of 32 transformation events comprising hpRNA specific for the 5126 gene promoter, 29 produced T1 plants that were male sterile.

Of 32 transformation events comprising hpRNA specific for the BS7 gene promoter, 23 produced T1 plants that either produced a small amount of non-viable pollen ("breaker" phenotype) or were male fertile but produced only a small amount of viable pollen ("shedder" phenotype).

Of 31 transformation events comprising hpRNA specific for the SB200 gene promoter, 13 produced T1 plants of either the breaker or shedder phenotype.

Of 24 transformation events comprising hpRNA specific for the PG47 gene promoter linked to a construct for herbicide resistance, 15 revealed no transmission of herbicide resistance to the T1 seedling when using pollen from the primary transformants. This is consistent with expected post-meiotic expression of PG47.

Anther RNA from plants expressing the various hpRNAs was analyzed by northern blot. For each target, six independent events were analyzed in the T1 generation to determine whether hpRNA expression reduced steady state RNA levels of the targeted genes. Anthers were staged at tetrad release to early uninucleate stage of microspore development. Poly $A^+$ RNA was isolated, separated by electrophoresis, transferred to membranes, and hybridized sequentially with probes specific for MS45, 5126, BS7, SB200, NOS, and actin (RNA loading control). No MS45, 5126, or BS7 transcripts were detected in plants expressing hpRNA specific for these endogenous promoters. Only a slight reduction of SB200 RNA was observed in plants expressing SB200 hpRNA.

Protein immunoblot analysis of anther proteins also was performed essentially as described previously (Cigan, et al., (2001) *Sex Plant Reprod.* 14:135-142). For each target, six independent events were analyzed in the T1 generation to determine whether expression of the promoter hpRNA reduced steady-state protein levels of the targeted genes. Anthers were staged as above, ground in Laemelli buffer, separated by electrophoresis, and reacted sequentially with antibodies specific for MS45, BS7, SB200 or 5126 protein. Similar to the northern blot results, no MS45, 5126, or BS7 proteins were detected in plants expressing hpRNA specific for these endogenous promoters, and only a slight reduction of SB200 protein was observed for events comprising hpSB200.

These results demonstrate that expression of promoter hpRNA can selectively suppress endogenous gene expression in plant cells. In addition, the results demonstrate that suppression of different genes involved in male sterility of plants can variously affect the plant phenotype, including the degree of male fertility.

EXAMPLE 2

Expression of Exogenous MS45 Gene Product Restores Fertility

This example demonstrates that plants rendered male-sterile by expression of an MS45 promoter hairpin construct can be restored to fertility by expression of an exogenous MS45 gene construct.

Constructs were prepared containing the MS45 coding sequence operably linked to a heterologous ubiquitin (UBI), 5126, SB200 or BS7 promoter; these constructs were introduced into ms45 ms45 plant cells. Regenerated plants and their progeny were fertile, demonstrating that the native promoter of MS45 can be replaced with either a constitutive or anther-preferred promoter to confer a male-fertile phenotype to mutant ms45 maize. (See also, Cigan, et al., (2001) *Sex Plant Reprod.* 14:135-142).

Further, plants containing the UBI:MS45 or 5126:MS45 construct were crossed to plants that were male sterile due to expression of an MS45 gene promoter hpRNA. Progeny were tested by PCR for presence of the hp construct and either UBI:MS45 or 5126:MS45. RNA hybridization analysis was conducted and fertility phenotypes were scored.

Northern blot analysis of RNA obtained from leaves of the progeny plants revealed that MS45 was expressed from the ubiquitin promoter in 7 of 12 hp-containing progeny obtained from the UBI:MS45 cross. Further, expression of MS45 from the UBI promoter correlated with observed fertility in the progeny plants. These results demonstrate indicate that MS45 is expressed from the constitutive ubiquitin promoter, and that constitutive expression of the MS45 gene product confers male fertility in the progeny plants.

Further, anther RNA from these MS45hp maize plants containing 5126:MS45, BS7:MS45, or UBI:MS45 was analyzed. Anthers were staged at tetrad release to early uninucleate stage of microspore development, and poly A+ RNA was collected, electrophoresed and hybridized sequentially with probes for MS45, SB200, and BS7. MS45 was expressed in anthers of the male-fertile progeny plants whether driven by the constitutive UBI promoter or by the anther-specific 5126 or BS7 promoters, with timing of anther collection likely affecting strength of the signal. No MS45 RNA was observed in the male-sterile hairpin-only containing plants. These results demonstrate that suppression of MS45 expression due to the MS45 hpRNA can be overcome by expressing MS45 from a heterologous promoter that drives expression at least in anther cells.

The promoter expressing the MS45 gene can be derived from a source other than maize, and can be, for example, any plant promoter capable of transcribing MS45 such that expression of the transcription unit renders plants male fertile. For example, the rice and *Arabidopsis* homologs of the maize MS45, 5126, BS7 and MS26 genes have been isolated and identified. Overall there is significant similarity between the coding regions, with conservation of the intronic regions. Importantly, the corresponding promoters of rice and maize are approximately 50 to 60% identical, suggesting that these promoters may function sufficiently in maize tapetum to transcribe the MS45 gene. To test this, each of the rice MS45, rice BS7, rice MS26 and *Arabidopsis* 5126 promoters was fused to the maize MS45 coding region and tested for ability of the construct to confer fertility when transformed into ms45 ms45 mutants. Using this test system, a high frequency of male fertile plants was observed for all four constructs.

In certain respects, it is advantageous to use non-maize promoters to express the MS45 gene. For example, where promoter hpRNAs from the same species reduce target gene function such that the plant is non-viable or non-reproductive, a promoter from a different species can be used to transcriptionally express the complementing gene function (e.g., MS45), thus circumventing this potential problem. Moreover, hpRNA constructs can be generated to target the non-maize promoters to suppress MS45 gene expression as a means to reduce or abolish function and render the plant male sterile by targeting the non-maize promoter used in the MS45 expression cassette. For example, an ms45 homozygous recessive plant may be transformed with an MS45 rice promoter homolog driving expression of the MS45 gene (MS45r::MS45), rendering the plant male fertile. To suppress expression of this MS45r::MS45 cassette, a second maize plant can be generated which is heterozygous for the maize MS45 mutation and expresses an MS45r promoter hpRNA. As there are no equivalent endogenous MS45 rice promoter target sequences in this maize plant, this plant would be male fertile. This second plant can be crossed onto the homozygous ms45 plant containing the MS45r::MS45 construct, and progeny screened for the MS45r::MS45 and the MS45r hpRNA constructs. In this situation, MS45r::MS45 gene function is suppressed by the presence and expression of the MS45rHP, resulting in a male-sterile plant.

Use of such constructs is supported by the finding that expression of the rice 5126 promoter hp in maize does not result in male sterile plants. This is in contrast to the results obtained using a maize 5126 promoter hp (see, Example 1) and suggests that expression of the rice 5126 promoter hairpin is incapable of suppressing the endogenous maize 5126 gene.

Taken together, the present Examples demonstrate that endogenous plant fertility genes can be inactivated using hpRNA mediated suppression, and that a fertile phenotype can be restored in phenotypically sterile plants.

EXAMPLE 3

Promoter Specific Hairpin RNA Suppresses Transmission of Transgene Mediated Herbicide Resistance This example demonstrates that pollen of plants hemizygous for a UBI:PG47 hairpin construct is non-viable as determined by non-transmission of herbicide resistance to T1 outcrosses when a herbicide resistance gene is linked to the PG47 hairpin construct.

An hpRNA specific for the PG47 gene promoter comprising an inverted repeat of the PG47 gene promoter driven by a ubiquitin promoter (UBI:PG47hp), linked to a 35S:PAT construct, was introduced into plant cells. Pollen from plants expressing the transgene, representing 24 low- or single-copy transformation events, was carried to ears of wild-type maize plants. Seed set on the ears was very good, and comparable to that observed when wild-type pollen was used. For each event, 32 seeds were planted in soil, and seedlings were sprayed 5 days post-germination with 2× LIBERTY herbicide to detect transmission of UBI:PG47hp linked to 35S:PAT.

It was expected that if PG47-specific hpRNA functioned at the post-meiotic division of microspores, then viability would be normal, and 50% of the pollen would carry the transgene, providing herbicide resistance in 50% of the progeny. However, if PG47 function is required for pollen viability, and the hairpin construct can suppress expression of the PG47 gene product, then 50% of the pollen grains would be non-viable; all viable pollen would lack the transgene and be incapable of transmitting herbicide resistance. Non-functioning UBI:PG47hp constructs would be detectable by the presence of herbicide resistant plants.

Fifteen of 24 events tested were herbicide sensitive. This result demonstrates that the UBI:PG47hp constructs suppress PG47 gene expression in pollen, rendering 50% of the pollen non-viable and preventing transmission of herbicide resistance operably linked to the suppression construct.

EXAMPLE 4

Plants Containing Multiple Promoter Specific Hairpin RNAs Suppress Multiple Target Promoters Plants containing 5126HP (i.e., a transgene encoding a 5126 promoter hpRNA) are used as pollen recipients for pollen from BS7HP expressing plants. In plants containing both 5126HP and BS7HP, endogenous expression of 5126 and BS7 is suppressed, leading to a stronger sterility phenotype than observed with either construct alone. Plants are selected to contain either the 5126HP or BS7HP or both and advanced to maturity, and the fertility phenotypes of these resultant plants are determined.

Alternatively or in addition to crossing as a means to combine hairpin constructs, one of said constructs, for example the 5126HP, can be placed under the transcriptional control of an inducible promoter. In the absence of induction, these BS7HP-containing plants are capable of producing enough pollen to self. However, upon induction of the 5126HP, these plants are male sterile, and can be used as females during hybrid production. This process depends upon the combined expression of the hairpin constructs (HPs) to render a plant infertile, while expression of only one of the HPs does not impart sterility.

In certain embodiments, expression of both hpRNAs can be placed under the transcriptional control of a single promoter. In this scenario, the hpRNAs can be designed to contain multiple target promoters within the same encoded RNA. For example, the 5126 promoter region can be juxtaposed to the BS7 promoter region and placed under the transcriptional control of a single ubiquitin promoter or other constitutive, developmental or tissue preferred promoter, resulting in the expression of an RNA containing a 5126 and BS7 hybrid hairpin that directs the suppression of both 5126 and BS7 endogenous genes. Any combination and number of various promoters that target multiple and different promoters can be used in the scheme. For example, a promoter that regulates plant height genes and a promoter important to a reproductive process can be combined, resulting in sterile plants having short stature.

EXAMPLE 5

Inbred Maintenance and Hybrid Production of Plants Containing Promoter-Specific Hairpin RNAs Suppressing Target Promoters and Complementation Constructs This example demonstrates how an inbred plant containing two constructs, a dominant hairpin RNA (hpRNA) construct specific for a promoter and an MS45 gene expressed from a tissue specific promoter, can be maintained and used in the production of male sterile females for hybrid production.

Inbred plants A1 and A2 are both homozygous recessive ms45 ms45. Fertility is restored to inbred A1 plants by introduction of a transgene expressing the MS45 coding region using the 5126 promoter. The A1 inbred plants also contain a BS7HP expressing construct. These plants can be selfed and maintained independently of inbred A2. In inbred A2 plants, fertility is restored by expressing the MS45 coding region using the BS7 promoter. The A2 inbred plants also contain a 5126HP expressing construct. These plants can be selfed and maintained independently of inbred A1 plants.

To generate seed for female inbreds for hybrid production, inbred A1 is detasseled and fertilized using pollen from inbred A2. The resultant seed from this cross is planted and all of the progeny plants are male sterile due to the presence of the homozygous ms45 alleles and the 5126HP and BS7HPs suppressing the fertility restoration genes, 5126-MS45 and BS7-MS45, respectively. These plants are used as females in hybrid production and pollinated with plants having wild-type MS45 gene resulting in hybrid F1 seed. All plants derived from this seed are heterozygous for the MS45 gene and are therefore male fertile.

This example demonstrates that plants containing both dominant suppression and restoring constructs can be maintained and used in a hybrid seed production strategy to generate sterile female inbreds and fertile hybrid plants.

EXAMPLE 6

Utility of Plants Containing Promoter Specific Hairpin RNAs Suppressing Target Pollen-Specific Promoters and Ms45 Complementation Constructs for Hybrid Production and Inbred Maintenance This example demonstrates how a method comprising the use of two constructs, a dominant hairpin RNA (hpRNA) construct specific for a pollen-specific promoter and a restoring transgene, allows for the propagation of a plant having a homozygous recessive reproductive trait without losing the homozygous recessive condition in the resulting progeny, for use in the production of sterile plants for hybrid production. This is accomplished by introducing into a plant at least one restoring transgene construct, operably linking a first nucleotide sequence comprising a functional copy of a gene that complements the mutant phenotypic trait produced by the homozygous recessive condition with a second functional nucleotide sequence which interferes with the formation, function, or dispersal of the male gametes of the plant. This construct is maintained in the hemizygous state and a plant containing such a construct is referred to as a maintainer. Interference with the formation, function, or dispersal of the male gamete may be accomplished by linking the sequences interfering with formation, function, or dispersal of the male gamete with a gamete-tissue-preferred promoter. Since the transgene is in the hemizygous state, only half of the pollen grains produced contain the restoring transgene construct and none of these are viable due to the action of the second gene that prevents the formation of viable pollen. Therefore, when the maintainer plant containing such a linked construct is used as a pollen donor to fertilize the homozygous recessive plant, the only viable male gametes provided to the homozygous recessive plant are those which contain the recessive allele, but do not contain any component of the transgene construct. The progeny resulting from such a sexual cross are non transgenic with respect to this transgene construct.

While no viable pollen produced by the maintainer contains the restoring transgene construct, 50% of the ovules (the female gamete) will contain the restoring transgene construct. Therefore, the maintainer can be propagated by self-fertilization, with the restoring transgene construct segregating such that it will be contained in 50% of the seed of a self fertilized maintainer. By linking the restoring transgene construct with a selectable marker, the 50% of the seed containing the transgene can be isolated to propagate the maintainer population, which remains homozygous for the recessive gene and hemizygous for the restoring transgene construct. In this scenario, a single inbred can be maintained.

Inbred A1 is homozygous recessive for the fertility gene ms45. Inbred A1 plants contain a construct in which male fertility is restored by expressing the MS45 coding region using a tissue specific promoter, for example the native MS45 promoter. Inbred A1 plants also contain a hairpin construct targeted to suppress a pollen expressed promoter, in this example, a PG47HP expressing construct operably linked to the MS45 restoring construct; and a selectable or screenable marker, for example, a marker that confers herbicide resistance and/or a construct that serves as a visual or detectable marker for plant and/or seed screening. These plants are fertile and can be selfed and maintained. The seed on these plants will segregate 50:50 for the transgene because only non-transgenic pollen is viable and capable of effecting fertilization of an ovule, 50% of which contain the construct.

To generate seed for female inbreds for hybrid production, in one row, only non-transgenic plants from inbred A1 are maintained; these plants are homozygous recessive ms45 and male sterile. In an adjacent row, both transgenic and non-transgenic plants from inbred A1 are grown. Fertility in this row segregates one to one (fertile to sterile); fertile plants are used to pollinate the sterile plants in the adjacent row. The seed from this cross is non-transgenic for the operably linked restorer, the hpRNA and the screenable marker constructs, and all of the progeny are male sterile due to the presence of the homozygous ms45 allele. These plants are used as females in hybrid production and pollinated with plants having wild-type MS45 gene resulting in hybrid F1 seed. All plants derived from this seed are heterozygous for the MS45 gene and, therefore, male fertile.

This example demonstrates that plants containing a dominant pollen suppression hairpin construct and a fertility restoring construct can be maintained as inbreds and used in a hybrid seed production strategy to generate sterile female inbreds and fertile hybrid plants.

EXAMPLE 7

Combinations

Two or more construct components described herein may be combined in various ways to create systems for controlling gene expression. Such combinations may be made by linking said components within a single vector, by using multiple vectors in simultaneous or sequential transformations, and/or by breeding of plants comprising one or more components. Possible components are described below and in Table 1. Table 2 provides representations of illustrative, but not exhaustive, combinations useful in controlling male fertility.

For example, the components may include promoters or coding regions other than those listed, and the order of the components within the constructs may be different than those shown. Further, a construct could comprise individual promoter/coding sequence combinations, or one promoter driving transcription of multiple coding sequence components. As an example of the latter, a construct could comprise a constitutive promoter driving transcription of an MS45 coding sequence as well as a polynucleotide encoding a gene product involved in producing or regulating a screenable marker (for example, pigment) to create a fusion product. This would allow screening for transformants using any tissue of the plant, while expression of the MS45 results in male fertility.

Within any of the constructs, one or more promoter hairpin components could be included, for example within an intron of any of the encoded genes, or within a 5' or 3' non-coding region, or as an initial or terminal extension. A hairpin may target a single promoter, or two or more promoters, within a single transcribed RNA. Pollen-promoter hairpin configurations, and/or polynucleotides encoding pollen-disrupting polypeptides, can serve to prevent transgene transmission through the male gametes.

Pollen-preferred or pollen-specific promoters ("Poll-P") include, for example, PG47, P95 (onset between mid- and late-uninucleate stages; see, SEQ ID NO: 2), and P67 (profile similar to P95, more highly expressed at mid-uninucleate stage; see, SEQ ID NO: 1).

Tapetum-specific ("Tisp-P") or tapetum-preferred ("Tap-P") promoters include, for example, MS45 (U.S. Pat. No. 6,037,523); 5126 (U.S. Pat. No. 5,837,851); Bs7 (WO 02/063021); and SB200 (WO 02/26789).

Other tissue-specific or tissue-preferred promoters useful in the invention include, for example, Br2 (*Science* 302(5642):71-2, 2003), CesA8, and LTP2 (*Plant J* 6:849-860, 1994).

Constitutive promoters ("ConstP") include, for example, the CaMV 35S promoter (WO 91/04036 and WO 84/02913); and the maize ubiquitin promoter.

Male fertility genes ("MF") useful in the invention include, for example, MS45 (Cigan, et al., (2001) *Sex. Plant Repro.* 14:135-142; U.S. Pat. No. 5,478,369) and MS26 (US Patent Application Publication Number 20030182689).

Pollen ablation genes ("Cytotox") useful in the invention include DAM (GenBank J01600, *Nucleic Acids Res.* 11:837-851 (1983); alpha-amylase (GenBank L25805, *Plant Physiol.* 105(2):759-760 (1994)); D8 (*Physiol. Plant.* 100(3): 550-560 (1997)); SacB (*Plant Physiol.* 110(2):355-363 (1996)), lipases and ribonucleases. In this regard, a single polypeptide, or a fusion of two or more polypeptides to generate a fusion product, is contemplated. Selectable marker systems useful in the practice of the invention include, for example, herbicide resistance conferred by PAT or MoPAT.

Screenable marker systems useful in the practice of the invention, for example in identifying transgenic seed among progeny of a selfed maintainer line, include GFP (Gerdes, (1996) *FEBS Lett.* 389:44-47; Chalfie, et al., (1994) *Science* 263:802), RFP, DSred (Dietrich, et al., (2002) *Biotechniques* 2(2):286-293), KN1 (Smith, et al., (1995) *Dev. Genetics* 16(4):344-348), CRC, P, (Bruce, et al., (2000) *Plant Cell* 12(1):65-79, and Sugary1 (Rahman, et al., (1998) *Plant Physiol.* 117:425-435; James, et al., (1995) *Plant Cell* 7:417-429; U18908).

Hairpin configurations may comprise, for example, PG47hp, P95hp, or P67 hp. A hairpin may target a single promoter or may target two or more promoters by means of a single transcribed RNA. The hairpin could be located in any appropriate position within the construct, such as within an intron of any of the encoded genes or within 5' or 3' non-coding regions.

TABLE 1

| Symbol | Description | Example |
|--------|-------------|---------|
| Poll-P | Pollen Promoter | PG47, P95, P67 |
| Tisp-P | Tissue Specific Promoter | Br2, CesA8, LTP2 |
| Tap-P | Tapetum Promoter | Ms45, 5126, Bs7, Sb200 |
| ConstP | Constitutive Promoter | 35S, Ubi |
| MF | Fertility Gene | Ms45, Ms26 |
| Cytotox | Cytotoxic Gene | DAM, Alpha-Amylase, D8, SacB |
| Herb R | Herbicide Resistance | PAT, MoPAT |
| Screen | Screenable Marker | RFP, GFP, KN1, CRC, Su1 |
| HP | Hairpin | PG47hp, P95hp, P67hp |

TABLE 2

| Description | Components |
|-------------|------------|
| Single cytotox + Selection | Poll-P:Cytotox/Tap-P:MF/ConstP:Herb R |
| Single cytotox + Selection + Screen | Poll-P:Cytotox/Tap-P:MF/ConstP:Herb R/Tisp-P:Screen |
| Double cytotox + Selection | Poll-P:Cytotox/Poll-P:Cytotox/Tap-P:MF/ConstP:Herb R |
| Single cytotox + Screen | Poll-P:Cytotox/Tap-P:MF/Tisp-P:Screen |
| Double cytotox + Screen | Poll-P:Cytotox/Poll-P:Cytotox/Tap-P:MF/Tisp-P:Screen |
| Hairpin + Single cytotox + Selection | ConstP:HP/Poll-P:Cytotox/Tap-P:MF/ConstP:Herb R |
| Hairpin + Single cytotox + Screen | ConstP:HP/Poll-P:Cytotox/Tap-P:MF/Tisp-P:Screen |
| Hairpin + Selection | ConstP:HP/Tap-P:MF/ConstP:Herb R |

TABLE 2-continued

| Description | Components |
|---|---|
| Hairpin + Screen | ConstP:HP/Tap-P:MF/Tisp-P:Screen |
| Hairpin/Male fertile fusion + Screen | ConstP:HP + MF/Tisp-P:Screen |
| Hairpin/Male fertile fusion + Selection | ConstP:HP + MF/ConstP:Herb R |
| Embedded Hairpin/Male fertile + Selection | ConstP:MF Embedded HP/ConstP:Herb R |
| Embedded Hairpin/Male fertile + Screen | ConstP:MF Embedded HP/Tisp-P:Screen |
| Embedded Hairpin/Screen | Tap-P:MF/ConstP:Screen Embedded HP |
| Single Cytotox Embedded Hairpin/Screen | Poll-P:Cytotox/Tap-P:MF/ConstP:Screen Embedded HP |
| Constitutive Fertility/Screen with Embedded Hairpin | ConstP:(MF + Screen) Embedded HP<br>Tap-P:Cytotox/ConstP:(MF + Screen) Embedded HP |

EXAMPLE 8

Visual Marker-Based Selection

The experiments described below were designed to ask whether the maize p1 gene, when expressed from various non-p1 promoters, could be used as a visual marker for seed carrying a linked transgene. As part of the experimental design, coloration of seed from the transformed plant, as well as coloration of seed generated by outcrossing pollen from the transformed plant, was tested to examine inheritance of maternal and paternal p1 gene expression.

The p1 gene of maize is a Myb-related transcriptional activator demonstrated to regulate the a1 and c2 genes to produce 3-deoxy flavonoids, such as C-glycosyl flavones, 3-deoxyanthocyanins, flavan-4-ols and phlobaphenes (Grotewold, et al., (1991) *PNAS* 88:4587-4591). Synthesis of these and related compounds results in the coloration of floral organs including pericarp, cob, silks, husks and tassel glumes (Cocciolone, et al., (2001) *Plant J* 27(5):467-478). Typically, expression of this gene is maternal; that is, outcrossing of the p1 gene does not confer coloration to reproductive parts until the next generation is grown from seed. As the p1 gene has been shown to confer color to non-reproductive maize tissues by constitutive expression in BMS (Black Mexican Sweet) cells (Grotewold, et al., Pl Cell 1998), expression of the p1 gene was investigated by placing the p1 gene under the transcriptional control of the maize seed-preferred promoters END2 and LTP2. Constitutive promoters rice Actin and maize Ubiquitin were also used to transcriptionally regulate the p1 gene. These vectors would test whether expression of the p1 gene would confer color differences sufficient for use as a visual marker.

The following vectors were introduced into maize by *Agrobacterium* transformation and tested for seed color of both the transformed plant and ears pollinated with pollen from the transformed plants.

| | |
|---|---|
| 23030 | End2:P1-UbimoPAT |
| 23066 | Actin:P1-UBImoPat |
| 23069 | LTP2:P1-UBImoPat |
| 23528 | End2:P1-35SPAT |
| 23535 | LTP2:P1-35S:PAT |
| 23537 | UBI:P1-35S:PAT |

Transformation with PHP23030 and PHP23069 has produced plants demonstrating segregating colored seed both on ears of the primary transformed plants and on ears pollinated by pollen from these transformed plants. For PHP23030, 12 of the 14 independent events used for outcrossing demonstrated brown colored kernels segregating among the yellow kernels at nearly a 1:1 segregation ratio. Ears on the primary transformants were pollinated with pollen from non-transformed plants and the kernels on these ears also segregated brown:yellow kernels at nearly a 1:1 ratio. Identical results were observed with three of the four events generated with PHP23069.

Brown and yellow seed from 5 single-copy PHP23030 events were sorted and planted to test for germination of the brown seed and co-segregation of the linked herbicide resistance marker, 35SPAT, with the colored kernels. In this small test, the majority (>95%) of the brown seed produced herbicide resistant plants, whereas the 39 of the 40 seedlings germinated from yellow seed were herbicide sensitive.

Close examination of the brown seed from PHP23030 revealed that the aleurone layer fluoresced green, while the endosperm of brown seed from PHP23069 showed strong green fluorescence when compared to yellow segregating seed derived from the same ear. This is consistent with the observation of green fluorescence observed in BMS cells bombarded with 35S:P1 (Grotewold, et al., (1998) *Plant Cell* 10(5):721-740). Moreover, examination of the transformed callus with PHP23528 (End2:P1-35SPAT) and PHP23535 (LTP2:P1-35S:PAT) revealed, in contrast to untransformed GS3 callus, both PHP23528- and PHP23535-containing callus fluoresced green. The observation of green fluorescence in these transformed callus and the co-segregation of brown kernels with the herbicide selectable marker in transformed plants indicates that expression of p1 from at least seed-preferred promoters can be used as a visual marker to identify transformed maize tissues.

EXAMPLE 9

Alternatives for Pollen Cytotoxicity

As shown in Tables 1 and 2, disruption of pollen function may be accomplished by any of numerous methods, including targeted degradation of starch in the pollen grain or interference with starch accumulation in developing pollen. For example, a construct comprising the alpha-amylase coding region is operably linked to a pollen specific promoter. The native secretory signal peptide region may be present; may be removed; or may be replaced by an amyloplastid-targeted signal peptide. In other embodiments, a construct may comprise a pollen-specific promoter operably linked to a coding region for beta-amylase; or for a debranching enzyme such as Sugary1 (Rahman, et al., (1998) *Plant Physiol.* 117:425-435; James, et al., (1995) *Plant Cell* 7:417-429; U18908) or pullulanase (Dinges, et al., (2003) *Plant Cell* 15(3):666-680; Wu, et al., (2002) *Archives Biochem. Biophys.* 406(1):21-32).

For example, hairpin constructs are created which target the promoter of the maize Sugary1 gene. Due to loss of the starch debranching enzyme activity, sugary1 mutants display shrunken kernels. Constitutive expression of the promoter inverted repeat should cause loss of Su1 promoter activity and result in inherited altered kernel morphology.

Although the invention has been described with reference to the above example, it will be understood that modifications and variations are encompassed within the spirit and scope of the invention. Accordingly, the invention is limited only by the claims.

All publications and patent herein referred to are hereby incorporated by reference to the same extent as if each was individually so incorporated.

What is claimed is:

1. A promoter providing preferential expression of an operably-linked polynucleotide in developing pollen, comprising the sequence of SEQ ID NO: 1.

2. An expression cassette comprising the promoter of claim 1 and an operably-linked polynucleotide.

3. A transformation vector comprising the expression cassette of claim 2.

4. A plant stably transformed with the expression cassette of claim 2.

5. The plant of claim 4, wherein the plant is a monocot.

6. The plant of claim 5, wherein the monocot is maize, wheat, rice, barley, sorghum, or rye.

7. A transformed plant cell comprising the expression cassette of claim 2.

8. A method for selectively expressing a polynucleotide in a plant cell, the method comprising transforming a plant cell with the expression cassette of claim 2.

9. The method of claim 8 further comprising regenerating a stably transformed plant from the transformed plant cell.

10. The method of claim 9 wherein fertility of the transformed plant is impacted.

* * * * *